(12) United States Patent
Nowinski et al.

(10) Patent No.: US 6,701,173 B2
(45) Date of Patent: Mar. 2, 2004

(54) CURVED SURGICAL INSTRUMENTS AND METHOD OF MAPPING A CURVED PATH FOR STEREOTACTIC SURGERY

(75) Inventors: Wieslaw Lucjan Nowinski, Singapore (SG); Timothy Poston, Singapore (SG)

(73) Assignee: Kent Ridge Digital Labs, Singapore (SG)

( * ) Notice: Subject to any disclaimer, the term of this patent is extended or adjusted under 35 U.S.C. 154(b) by 58 days.

(21) Appl. No.: 08/945,474

(22) PCT Filed: Feb. 25, 1997

(86) PCT No.: PCT/SG97/00008

§ 371 (c)(1),
(2), (4) Date: Jul. 12, 1999

(87) PCT Pub. No.: WO97/31581

PCT Pub. Date: Sep. 4, 1997

(65) Prior Publication Data

US 2003/0149351 A1 Aug. 7, 2003

(30) Foreign Application Priority Data

Feb. 27, 1996 (SG) .............................................. 96 06118

(51) Int. Cl.[7] .................................................. A61B 5/05
(52) U.S. Cl. ........................ 600/407; 606/130; 434/262; 382/128
(58) Field of Search ................................ 600/407, 427, 600/382, 425, 429, 109, 111, 112, 104; 606/130, 108; 604/264, 280, 164, 116; 601/2, 46

(56) References Cited

U.S. PATENT DOCUMENTS 4,306,562 A * 12/1981 Osborne ..................... 128/348
4,386,602 A * 6/1983 Sheldon et al. ................. 128/4
4,552,554 A * 11/1985 Gould et al. .................... 604/51
4,563,181 A * 1/1986 Wijayarathna et al. ..... 604/280
4,681,103 A 7/1987 Boner et al. ................. 128/303
4,773,431 A * 9/1988 Lodomrski ................... 128/769

(List continued on next page.)

FOREIGN PATENT DOCUMENTS

| EP | 0160238 | 11/1985 |
| EP | 9206645 | 4/1992 |
| EP | 0682919 | 11/1995 |
| WO | 9428819 | 12/1994 |

OTHER PUBLICATIONS

Article entitled "Virtual Reality Software & Technology, Proceedings of the VRST '94 Conference, Aug. 23–26, 1994, Singapore".

Poston, T. et al. "The Virtual Workbench: Dextrous VR" Virtual Reality Software & Technology Proceedings of the VRST '94 Conference (Aug. 1994) pp. 111–121.

Primary Examiner—Eleni Mantis Mercader
(74) Attorney, Agent, or Firm—Ladas & Parry

(57) ABSTRACT

The method of mapping a curved path for stereotactic surgery involves the selection of a helical-shaped path. The first step is to obtain an accurate image of the pertinent structures of the patient's internal areas. The image includes the lesion or target region and a potential opening site. Using the image, the non-target areas surrounding the lesion area are determined and evaluated for the medical acceptability of passing through them. A curved path which is substantially helical in shape is then selected within the image such that the curve avoids these non-target areas but intersects the target region and the opening site. The corresponding surgical instrument which will be used to follow the selected curved path has a rigid body having a shape which is substantially identical to the path.

12 Claims, 36 Drawing Sheets

U.S. PATENT DOCUMENTS

| | | | |
|---|---|---|---|
| 4,869,247 A | * 9/1989 | Howard, III et al. | 128/303.1 |
| 4,883,474 A | * 11/1989 | Sheridan et al. | 604/280 |
| 4,986,814 A | * 1/1991 | Burney et al. | 604/164 |
| 5,045,072 A | * 9/1991 | Castillo et al. | 604/280 |
| 5,078,713 A | * 1/1992 | Varney | 606/23 |
| 5,163,430 A | 11/1992 | Carol | 128/653.1 |
| 5,171,296 A | 12/1992 | Herman | 602/5 |
| 5,191,898 A | * 3/1993 | Millar | 128/748 |
| 5,205,289 A | * 4/1993 | Hardy et al. | 128/653.1 |
| 5,217,466 A | 6/1993 | Hasson | 606/119 |
| 5,230,623 A | 7/1993 | Guthrie et al. | 433/72 |
| 5,342,371 A | 8/1994 | Welter et al. | 606/113 |
| 5,359,417 A | 10/1994 | Müller et al. | 356/21 |
| 5,394,457 A | 2/1995 | Leibinger et al. | 378/162 |
| 5,788,713 A | * 8/1998 | Dubach et al. | 606/130 |
| 6,390,097 B1 | * 5/2002 | Chandra | 128/898 |

* cited by examiner

CURVED SURGICAL INSTRUMENTS AND METHOD OF MAPPING A CURVED PATH FOR STEREOTACTIC SURGERY

FIELD OF INVENTION

This invention relates to the field of stereotactic surgery, and particularly to curved instruments and method of mapping a curved path for stereotactic surgery for situations where a straight path is impossible or would be more invasive or risky than a curved path.

BACKGROUND OF THE INVENTION

1. Nomenclature and Definition of Terms

Currently, stereotaxis is generally associated with neurosurgery, and particularly with intracranial surgery. However, in the following description, the terms "stereotaxis" or "stereotactic surgery" or "stereotactic surgical procedure" shall not be used in that limited sense; rather it should be understood that the term shall be used more generally to distinguish it from the "conventional" surgical procedures where a large incision is made in a patient. Hence, the terms "stereotaxis", "stereotactic surgery", "stereotactic surgical procedure" shall encompass those clinical procedures where a rigid instrument is inserted into a small opening and is navigated, by control of the part that remains outside, to a pre-determined area of a patient's body. However, frequent references will be made to intracranial surgery as a way of illustrating the invention and its mode of operation, and therefore, such references should not be construed as a limitation on the present invention.

2. Description of the Related Art

Stereotactic surgery (also known as "stereotaxis") is well known to those skilled in the art. It is a special surgical procedure for treating an interior portion of a patient, usually the brain and other intracranial structures, by inserting a rigid probe into a small opening. In conventional open surgery, the surgeon makes an incision large enough for the surgeon to see the path leading to the area of pathology. Stereotaxis, on the other hand, does not require the surgeon to actually see the entire path, so a small opening, only big enough to insert the probe, is required. Hence, stereotactic surgical procedures offer the advantage of minimizing the damage to the tissues surrounding the lesion area, and promotes faster recovery of the patient.

Because a surgeon performing stereotactic surgery does not directly view the inner portions of the brain, he must be able to map out a path and note the sensitivity of the tissues surrounding the damaged area. He must also be able to navigate the probe such that the position of the probe corresponds exactly with the designated path. To achieve the necessary control, a number of apparatus and methods have recently been developed. CAT scan technology, magnetic resonance imaging (MRI), angiography, digital subtraction angiography (DSA) and similar diagnostic procedures are currently used to obtain the visual image of the intracranial area. Such devices are coupled to apparatus, typically a rigid helmet-like framework worn on the skull, or (less invasively but less precisely) markers attached to the skin and 'frameless' guidance system or robot, which precisely positions the probe in accordance with the visual images.

Currently, only straight probes are used in stereotaxis. Hence, only a straight path leading to the selected point can be used. When choosing a straight path, the surgeon selects a path which best avoids sensitive areas or other obstructions. If the path meets a bone, an opening can often be formed by drilling a hole. But if the selected path meets blood vessels, nerves, or brain tissues with important brain functions, a different path must be chosen, or risk causing irreparable damage to the brain.

Not all areas can be reached via a straight path, however. Some sites are so well surrounded by important tissues that no straight path exists where the risk is low. In other situations, a straight path may exist, but the damaged area may be buried deep within the brain requiring a penetration through thick layers of tissues. In still other situations, the path may be confronted by a hard tissue such as calcified dura mater which the probe is unable to penetrate. Lesions in such unreachable places may either be classified as inoperable or be treated using the traditional open procedure.

In some of these situations, a curved path may better avoid the obstructions or sensitive tissues, and reach the intended area with lower risk to the patient. However, at the present, only straight devices are in use, which can follow only a straight path, unless they are allowed to move sideways and create a sheet of damage. To make only a line of damage, the body of the device must slide along the path pierced by the tip. For most curved instruments, however, such sliding movement along a designated curved path is difficult or impossible.

Hence, in light of these shortcomings, it would be desirable to have curved surgical instruments and a method of mapping a corresponding curved path which will not cause significant damage to the surrounding tissue, and which will allow a stereotactic procedure to become a viable option in a greater number of cases.

SUMMARY OF THE INVENTION

The method of mapping a curved path for stereotactic surgery involves the selection of a helical-shaped path. The first step is to obtain an accurate image of the pertinent structures of the patient's internal areas. The image includes the target region and a potential opening site. Using the image, the non-target or high-risk areas surrounding the target region are determined and evaluated for the medical acceptability of passing through them. A curved path which is substantially helical in shape is then selected within the image such that the curve avoids these regions. The corresponding surgical instrument which will be used to follow the selected curved path has a rigid body having a shape which is substantially identical to the path.

DETAILED DESCRIPTION OF THE INVENTION

Figure 1:
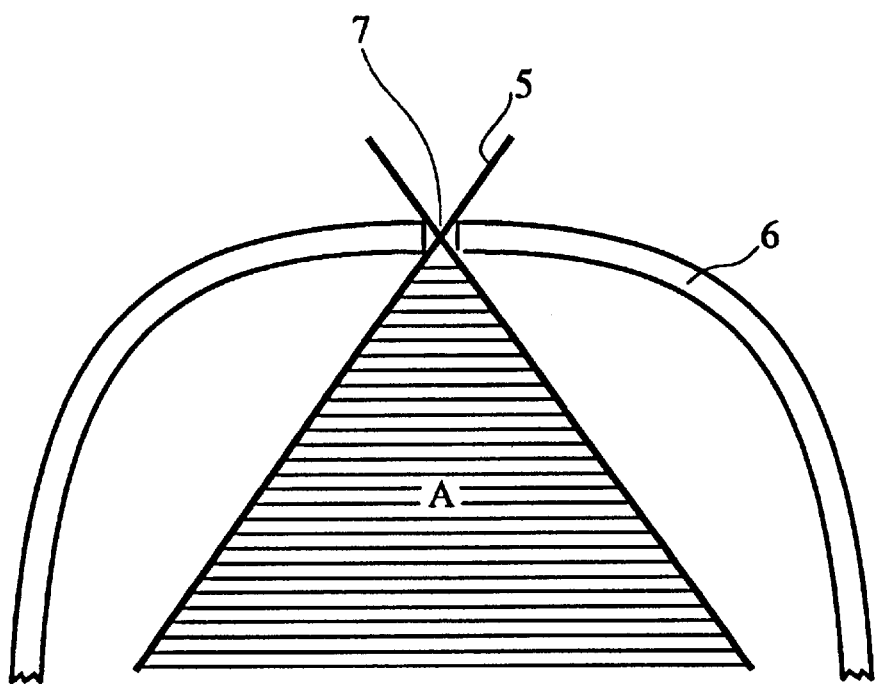
FIG. 1 shows the region of the brain accessible by a straight probe through a single hole in the skull.
Figure 2:
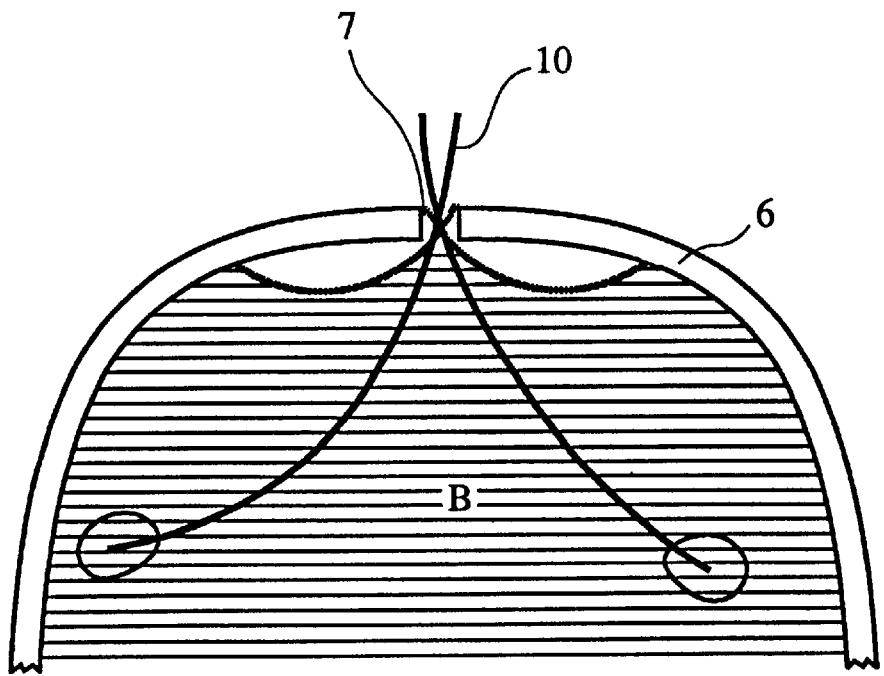
FIG. 2 shows the region of the brain accessible by curved probes through a single hole in the skull.

The present invention relates to a method of mapping a curved path for stereotactic surgery so a rigid curved instrument, having the same shape as the path, can be navigated to the intended area. The utilization of a curved path for stereotaxis offers a number of options and benefits unavailable for a straight instrument. Generally, the field of access is greatly increased for a curved path. FIG. 1 illustrates the field of coverage for a straight instrument 5 (the region marked A) which is inserted into the cranium 6 through a small opening 7. FIG. 2 illustrates the field of coverage for a curved instrument 10 (the region marked B) which is inserted into the same cranium 6 through the same opening 7. As demonstrated by these two figures, the curved instrument can be made to cover a greater area than a straight instrument. Hence, the availability of a curved path allows stereotactic procedure to become a viable option in greater number of situations.

Figure 3:
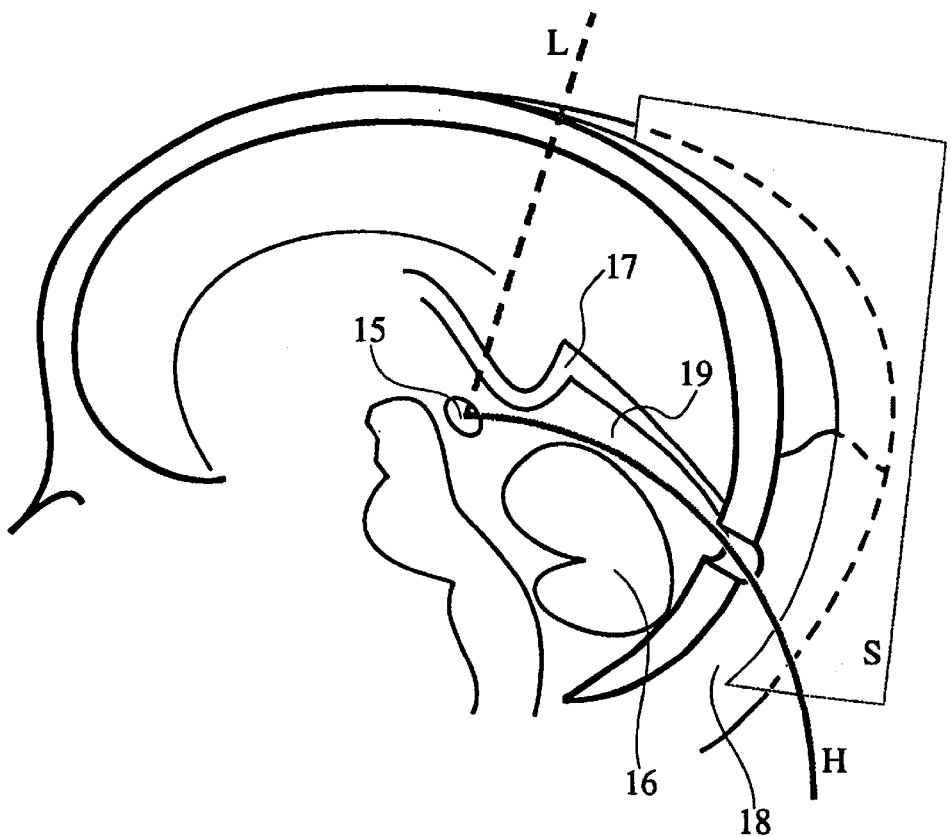
FIG. 3 is an image of the brain having a lesion located deep inside the brain, and curved access to it.

There are a number of situations where a curved path will be the preferred option because any straight path to the area to be accessed passes through a considerable amount of brain tissue. One such situation is illustrated in FIG. 3, where a lesion is located deep within the brain, in the pineal body 15. Here, along any straight path such as L, an instrument penetrates sensitive structures such as the cerebellum 16 or blood vessel 17, and risks serious damage. The curved path H enters the cranium 18 to the left of the mid-sagittal plane S and utilizes a less risky channel, via cerebrospinal fluid 19, to the lesion area.

Figure 4:
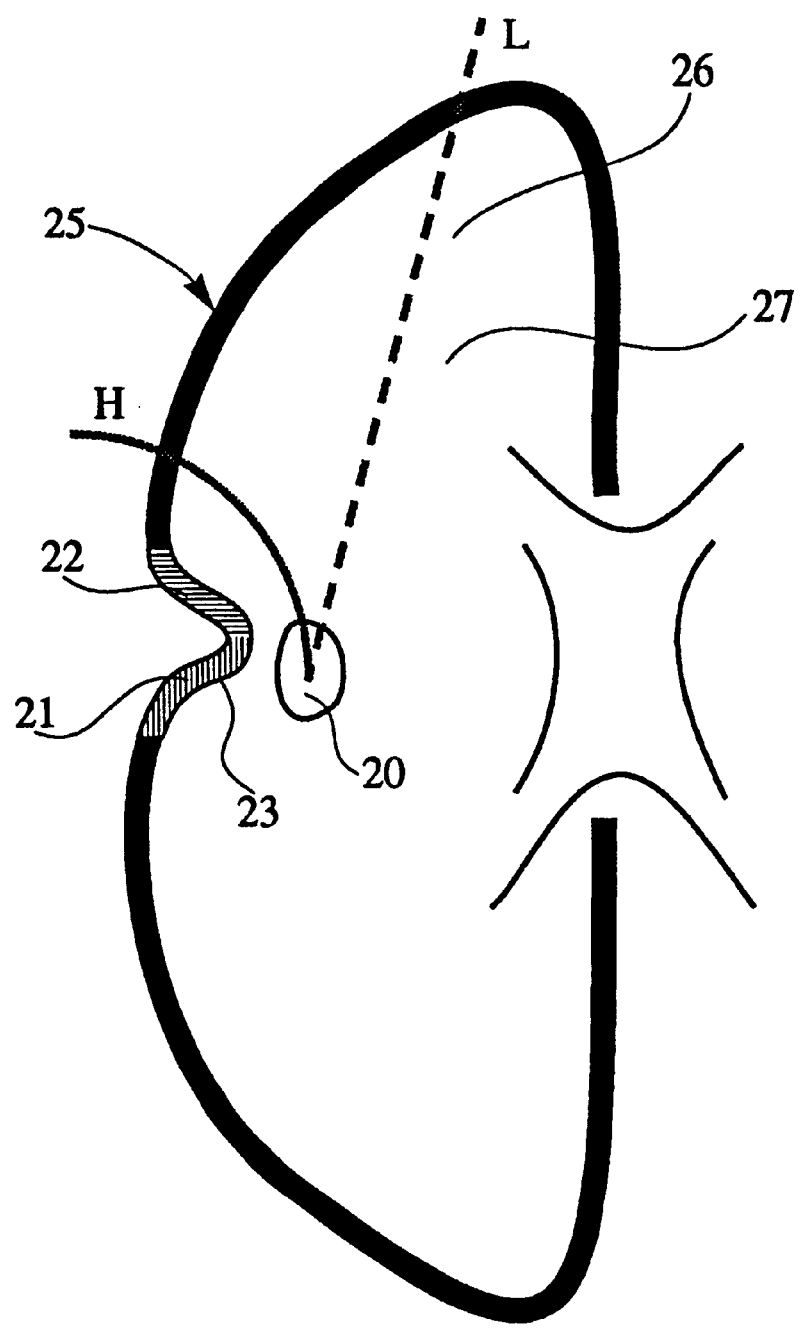
FIG. 4 is an image of the brain having a lesion near the cerebral cortex, in a region where cortex penetration is dangerous.
Figure 5:
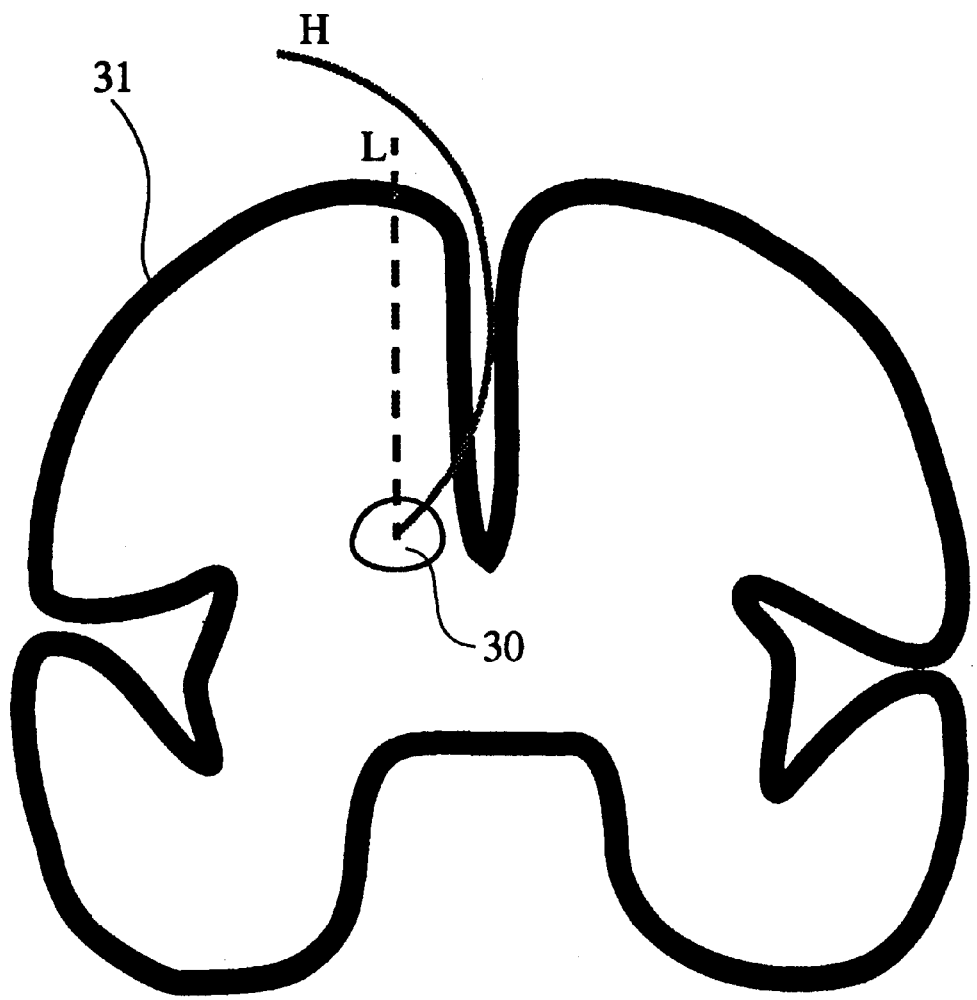
FIG. 5 is an image of the brain having a lesion closely beneath the folded cortex, where a curved probe meets less tissue than a straight one.

In other instances, a straight path may exist, but it would be more invasive than a curved path. A common situation exemplifying this principle is illustrated in FIG. 4. Here a tumor 20 lies fairly closely below the cerebral cortex 23 of the brain 25. A direct straight path would risk unacceptable damage to the sensory cortex 21 or motor cortex 22, and the consequential loss of sensation or control in the corresponding parts of the body. The current solution is to approach the tumor 20 via the path L, that is through the frontal lobe 26. This path passes through a great deal of white matter 27, with risk to the long-range connectivity of the brain that is hard to assess for the individual patient since the connection geometry is variable. If a curved path can be used, however, it can access the tumor via the path H, through the frontal lobe 26. This path meets far less brain tissue, and the frontal lobe 26 is currently the path of choice (for straight instruments) when accessing other target points. Similarly, in FIG. 5 a lesion 30 lies closely under the cortex 31 but cannot be reached by a straight path that passes quickly through the cortex 31; the curved path H can reach it more directly.

Figure 6:
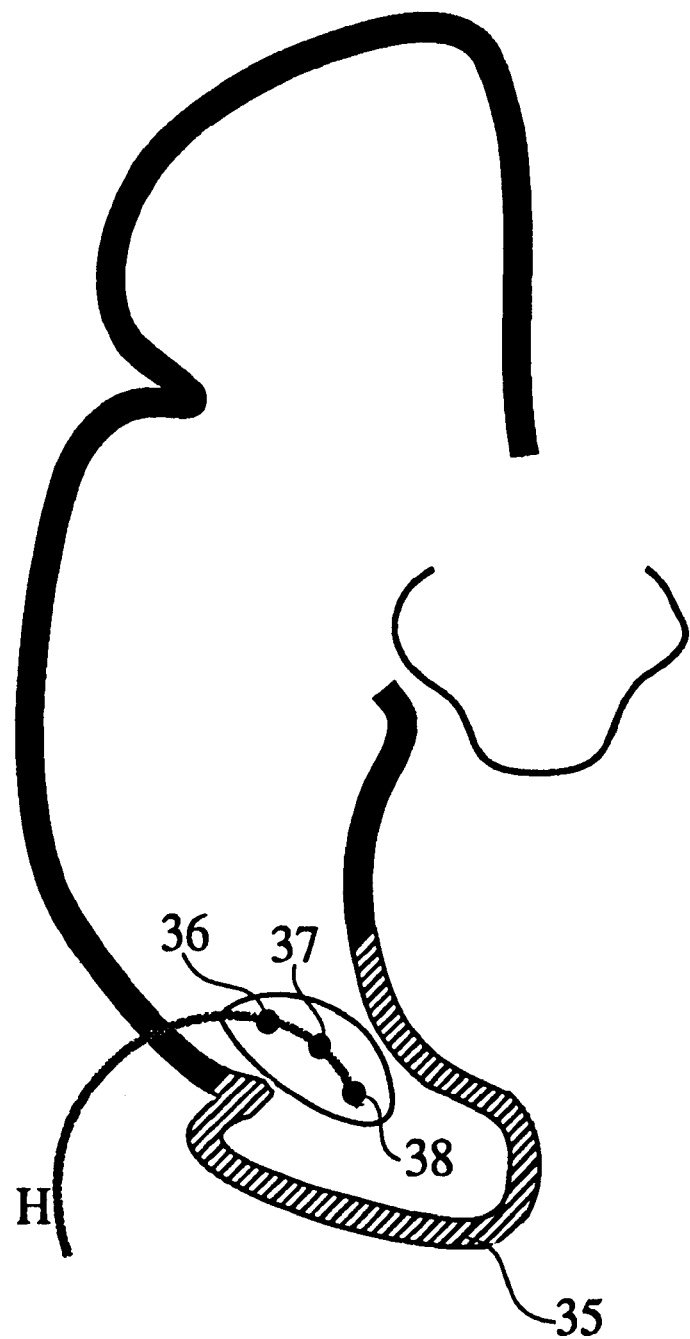
FIG. 6 is an image of the placement of drug or radiation sources at multiple sites in a lesion, which would require two straight penetrations but only one curved one.
Figure 7:
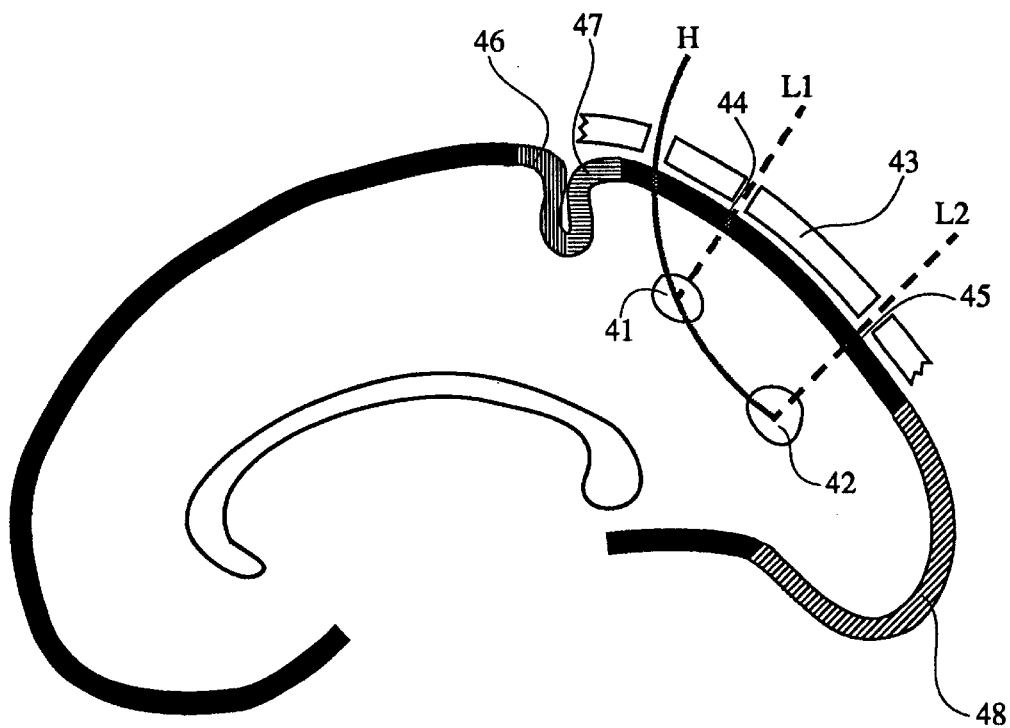
FIG. 7 is an image of the brain requiring biopsy at multiple sites, which would require two entry points for straight access but only one for curved access.

In still other situations, a straight path may simply be more labor-intensive. In FIG. 6, several drug or radiation sources, 36, 37, 38 can be placed by a single procedure along a curved path H, in a direction which would require a straight one to pass through the visual cortex 35. In FIG. 7, the two target sites 41 and 42, where scan data suggest a need for biopsy samples, are individually reachable but no acceptable straight path meets both. They thus require two openings in the cranium 43, and two separate brain penetrations, 44, 45, along straight paths L1 and L2. In contrast, the curved path H allows collection of material from both sites from a single opening, without meeting the motor cortex 46, the sensory cortex 47, or the visual cortex 48. This avoids the additional cost, risk, and effort of using two paths rather than one.

In FIG. 2, multiple penetrations are necessary even with a curved probe, but they can both use the same drill hole in the skull and pass through essentially the same place in the cortex, even though they go to widely divergent points. FIG. 2 shows the increased volume of the brain reachable through a single skull hole.

Figure 8:
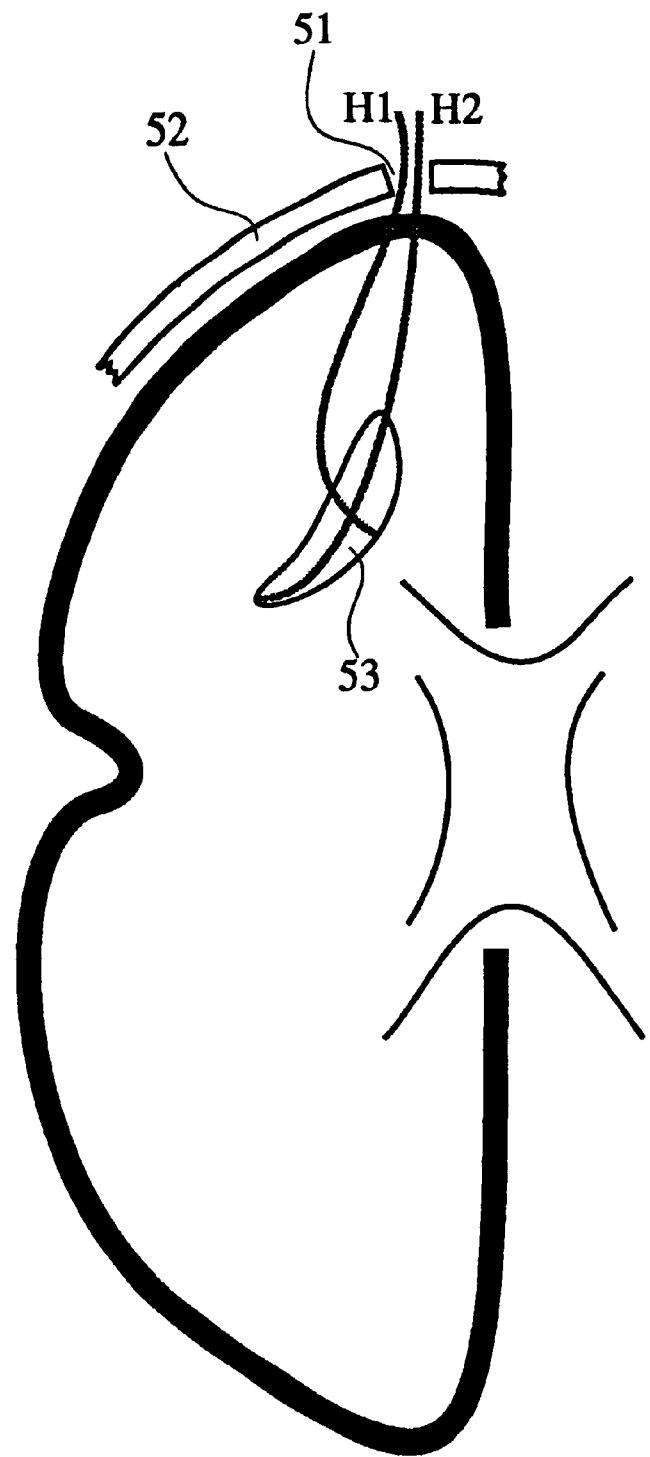
FIG. 8 shows biopsy access in more than one direction to the same lesion through a single hole, by curved paths.

FIG. 8 shows that with curved probes H1 and H2, a single opening 51 in the cranium 52 can suffice for biopsy of a suspect region 53 in multiple directions, mapping its extent in each.

In view of the figures above, the benefits of the curved path are multitudinous. But it should be understood that not every set of curved paths will be a viable option. In order for any curved path to be considered, the path must meet an important criterion. It is imperative that a rigid curved instrument having a shape identical to the shape of the path can be navigated through the brain matter without significantly deviating from the determined course. Specifically, the instrument must be able to travel along the path without cutting across the surrounding tissues. To make only a line of damage, the body of the rigid surgical instrument must slide along the path pierced by the tip. For most curved shapes, such rigid instrument sliding along a path is impossible; if a golf club form, for instance, slides along the line of its shaft, the head leaves a sheet of damaged points. If the head slides in its own direction, the shaft creates sideways damage. Hence, the curve must be such that the rigid instrument slides only along the path traced by its tip.

Figure 9:
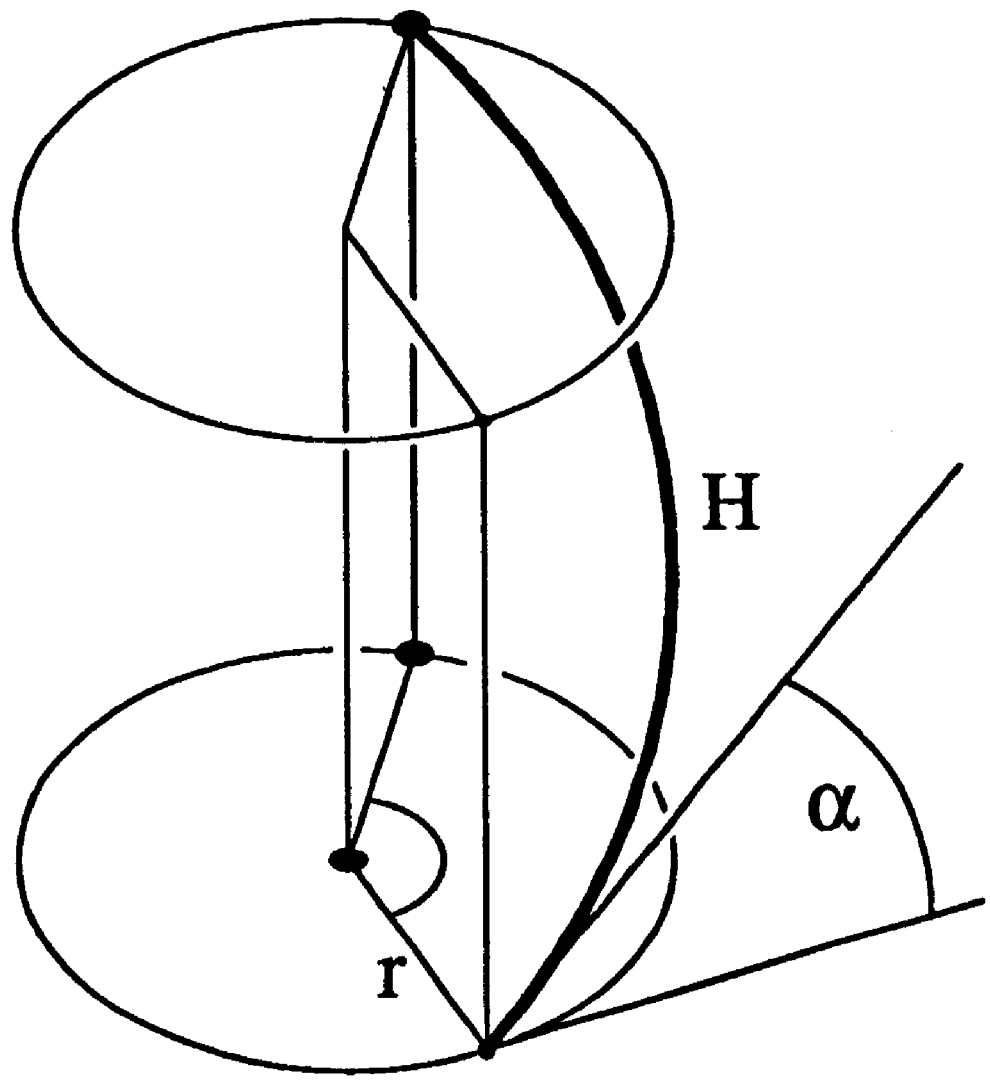
FIG. 9 shows the geometrical form of a helix.

To achieve this goal, the shape of the surgical instrument, and hence, the shape of the path must be that of a helix. As illustrated in FIG. 9, helix H is a well-known shape which is defined as a curve wound evenly around an arbitrarily placed cylinder of constant radius r, making a constant angle α with the cylinder's axis. A helix has the characteristic in that as the angle α approaches 0 degrees, the helix approaches the limiting shape of a straight line. In the other extreme, as the angle α approaches 90 degrees, the helix approaches the limiting shape of a circular arc. Therefore, a straight line and a circular arc are a special case of the general form of a helix.

Figure 13:
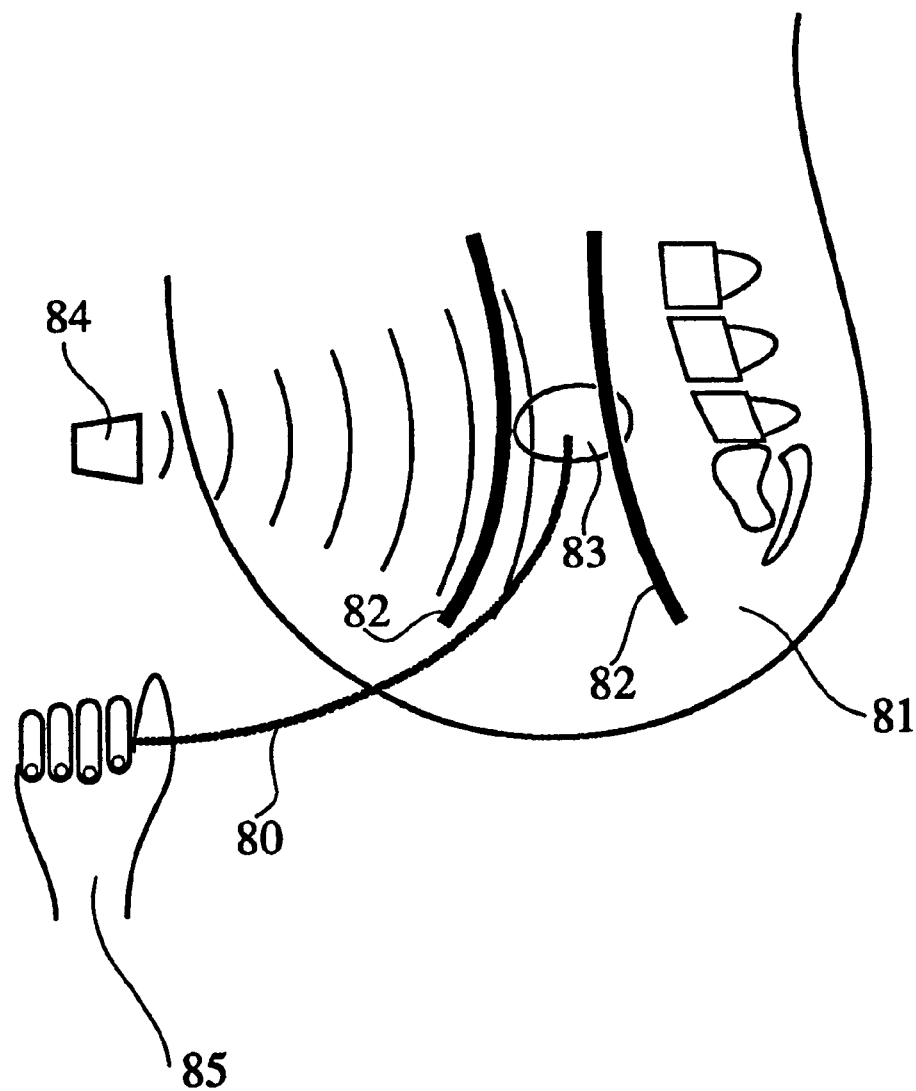
FIG. 13 shows a helical instrument being hand-guided through flexible tissue, where the user is assumed to have a continuously updated image of its position.

These two features, of motion with damage only at the tip, and of controllability by a fixed passive constraint, are consequences of the same 'slide along itself' property of the class of helical curves (including the degenerate straight and circular cases). They are both important where the precision of brain surgery is required, but in less complex tissues (where hand insertion guided by continuously updated images may be preferable to a pre-planned path), only the first is needed. In FIG. 13 the helical instrument 80 pushed by hand 85 is being guided through muscle 81 and avoiding blood vessels 82 for a target 83, guided by an ultrasound imaging system 84; it is not critical which part of the muscle tissue it meets, and muscle is sufficiently flexible that if the hand turns the instrument slightly, in a motion that is not merely a slide along the helix, the tissue can follow this sideways motion without tearing. The surgeon can then continue the sliding penetration, arriving more accurately at the target as a result of response to image feedback.

Although it is preferred that the shape of the path and the instrument be that of a near-perfect helix, some deviation is possible without substantial degradation of the useful properties of the helical shape. Some examples will be described for the purpose of illustrating this principle.

As described above, a perfect helix is a curve wound evenly around an arbitrarily placed cylinder of constant radius r, making a constant angle α with the cylinders axis. However, the shape may have slightly deviating r and/or angle α without substantially affecting the outcome, so long as the deviation is not excessive. The exact range of deviation which can exist without unduly affecting the effectiveness of the curved instrument, however, will vary depending on several factors such as the rigidity of the surgical instrument, the type of procedure being conducted, and the flexibility of the tissues being penetrated.

Further, it may be possible to deviate from a perfect helix to a greater extent where the deviation is periodic. An example would be a near-helical shape where the radius r and the angle α deviate by a fixed amount at an evenly-spaced interval, where at every other interval, the radius r and the angle α deviate oppositely to the one before.

In addition, it may be possible, and perhaps useful, to have a curved instrument only a portion of which has a helical shape. Other slight modifications, not specifically mentioned herein, may also be possible, so long as the general helical shape is intact.

In mapping the proper curved path having the helical shape, the first step is to generate an accurate medical image of the portion of the affected area of a human body. The image should cover all of the pertinent regions, and particularly the region to be accessed by the surgical instrument, the surrounding region, and potential entry sites.

A multitude of methods currently exists for obtaining medical images. Some common examples are scans using MRI, PET, CAT, plain radiographs, etc. Other means may include commercially prepared body maps or detailed 3-D models. Whichever the method, it must provide detailed information as to the respective location, shape, and size of the varying tissues, organs, blood vessels, and other important matters, such that a surgeon can determine the path which avoids the undesired regions.

Although the images obtained may be viewed in their original format, it is preferred that they be viewed in digitized form, and interfaced with other devices such as a computer or digital signal processor. In this way, they may be easily manipulated and superimposed with other images or otherwise manipulated for easy viewing.

After an accurate image is obtained, the region to be accessed, or target area, and some potential opening sites must be identified. The surrounding region is then observed and analyzed for sensitive tissues, organs, blood vessels, and other matters which need to be avoided by the surgical instrument. A helical curve is then superimposed onto the image such that the curve is able to access the desired region via one of the chosen opening sites without intersecting any of the sensitive areas. In choosing the path, it is useful to try a number of helices having different combinations of radius r and the angle α until a helix meeting all of the criteria is determined.

When selecting the path, it may be possible to have several helical curves which meet the criteria. In such a case, several factors may be considered in choosing the particular helical path which will be used for the surgical procedure. One important factor is the overall distance of the path through the tissue. Generally, the shorter the better. Another factor which may be considered is the pitch, or the acuteness of the angle α. It is generally preferred that the helix with the least acute angle α be chosen. A number of other factors may also be considered, such as the risks associated for a particular path taking into consideration the type and nature of the tissue in the regions the path will intersect.

To choose the optimal path, quantitative values may be assigned to these and other relevant factors. For each path using a particular helix, a total utility value may be assigned to each of the combinations. After a number of combinations is considered, the utility values may be compared, and the path-helix combination having the highest utility value may be chosen.

While the general method of mapping described above is useful, the medical potential of helical surgical instruments would be significantly diminished without a practical way to choose an access path appropriate to a patient's particular needs and his or her structural geometry, both of which vary. Successful choice requires a way to specify a particular path, a way to assess what tissues it meets, a way to see what change may improve an unsatisfactory choice, and a way to make such a change; all of which must be easy to use, to minimize errors and the time spent by the surgeon. The choice must then be translated easily and clearly into specific procedure in the operating room.

The 3-dimensional relation of path and data preferably requires a 3-D graphic display, which for ease of depth-perceptual judgment should be stereographic. Given a particular target point P, there are five degrees of freedom in selecting a helix ending at P, or six if a start is also chosen. This suggests control by the six degrees of freedom—three translational, three rotational—of an object held in space. Many control interfaces could be suggested by one skilled in the art; the essential is that the user should be able to move freely in the set of helices.

Within the display, since many important brain structures are not directly visible in a patient's scan data, there must be a labeled set of constructs aligned with the data as a guide to the patient's anatomy. No one such electronic brain atlas is an essential, but some electronic brain atlas should be included, together with software features evident to one skilled in the art, such as the highlighting and labeling of structures met by the current helix, and facilities to modify which ones are displayed and their transparency.

While there exists a number of ways to implement the above-described system, it is preferred that a virtual reality apparatus, such as the one described in the following publication be adopted: T. Poston and L. Serra, *The Virtual Workbench: Dextrous VR*, proceedings Association for Computing Machinery, Virtual Reality Software and Technology (ACM VRST) 1994, G. Singh, S. K. Feiner, D. Thalmann eds., World Scientific, 1994, pp. 111–122. This is an apparatus by which the user grasps a 6-degree-of-freedom sensor behind a mirror which reflects a stereographic display. A handle appears in the display precisely where the user's neuromuscular spatial sense reports that the sensor is currently held, and in the same orientation, so that the handle can be manipulated with hand-eye coordination, which is important for dextrous, intuitive control. In the display, the handle is equipped with a virtual tip whose shape depends on the tool function to which it is currently assigned. Either one or two sensors can be supported; in this case, it is useful to have such a handle in each hand. General functions like file management, selection and rotation of objects, etc., are provided by the software.

A number of approaches to selection of a path are possible, in which the use of six-degree-of-freedom user input is required to varying degrees. For the 'hand-held' method described below, it is essential; for the others it is helpful, but could be replaced by a more cumbersome 2-D mouse input. Since the range of physically available instrument geometries will always be finite, in most cases it will be necessary to find the available helix geometry nearest to that of the 'ideal' helix H, and adjust its position near H to satisfy the avoidance criteria.

Figure 14:
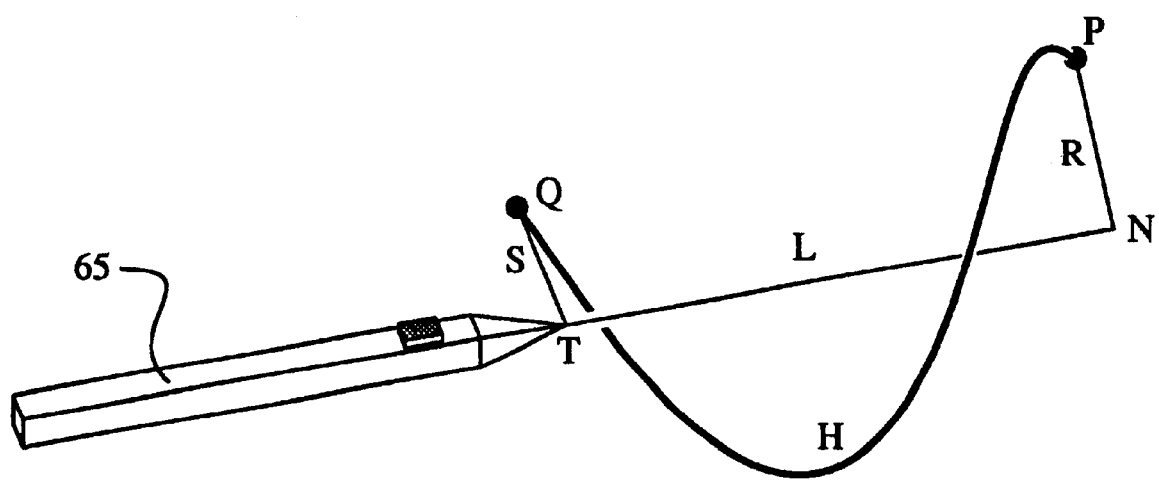
FIG. 14 is a mathematical diagram illustrating the formation of a helix using a virtual reality apparatus.

FIG. 14 illustrates one process for selecting a helical path using this apparatus. In the display, the user sees a virtual selection tool 65 whose displacement and movement correspond precisely with that of a sensor handle (not shown) which the user manipulates. The virtual selection tool has a tip which is used mark points of reference. The user first brings the virtual selection tool tip T to a target point P of interest within the display volume, and clicks a button on the sensor handle to mark the point. After the point P has been marked, the user can move the virtual selection tool to create a helical path having any combination of radius r and the angle α.

As shown in FIG. 14, the helix H is created around an imaginary cylinder having a unique set of parameters depending on the position of the tool tip T, and the direction in which the tool points. At any given position of tip T, a line L is formed (and preferably displayed) in the pointing direction, and L becomes the axis of the cylinder around which the helix H is to be wrapped. The radius R of the cylinder joins P to the nearest point N on L, and is continually redefined as the user moves the handle and thus redefines L. A tip radius line S (equal in length to R), is orthogonal to L; we define Q as the point where it meets the cylinder. Line S is initially parallel to R, but since it is rigidly attached to the virtual selection tool at the tip T, the point Q moves around the cylinder as the selection tool is twisted about its axis L. For each successive position of the tool (until the selection button is released, fixing the choice), a helix H is created and displayed which joins Q to P around the cylinder, with an amount of turn equal to the total angle that Q has traveled around L in the moving coordinate frame of the selection tool.

If v is the vector from T to Q, and w the vector from T to N, let u be the vector $$\frac{v \times w}{|w|}$$

orthogonal to both, and l be the length of L. H may be parametrised as the curve, $$H(t) = N + \cos(t)v + \sin(t)u + (t/l)w$$

or coordinates as, $$= (N_1 + \cos(t)v_1 + \sin(t)u_1 + (t/l)w_1,$$
$$(N_2 + \cos(t)v_2 + \sin(t)u_2 + (t/l)w_2,$$
$$(N_3 + \cos(t)v_3 + \sin(t)u_3 + (t/l)w_3),$$

from t=0 (giving the point P) to t=1 (giving the point Q), which may be displayed in the normal way for threedimensional curves; compute H(t) for a closely-spaced sequence of t values from 0 to 1, and call standard 3-D drawing routines (for instance, from the library OpenGL installed on many graphics machines) to project these points on the screen for a left or right view (both, when viewing is stereo), masked by 'Z-buffer' routines when the curve passes behind another graphical object.

Some other selection procedures, useful in particular circumstances, are listed below. It may sometimes be convenient for the surgeon to make an initial specification by one procedure, such as the one just described, and then make fine adjustments using another, such as one of the following.

Figure 15:
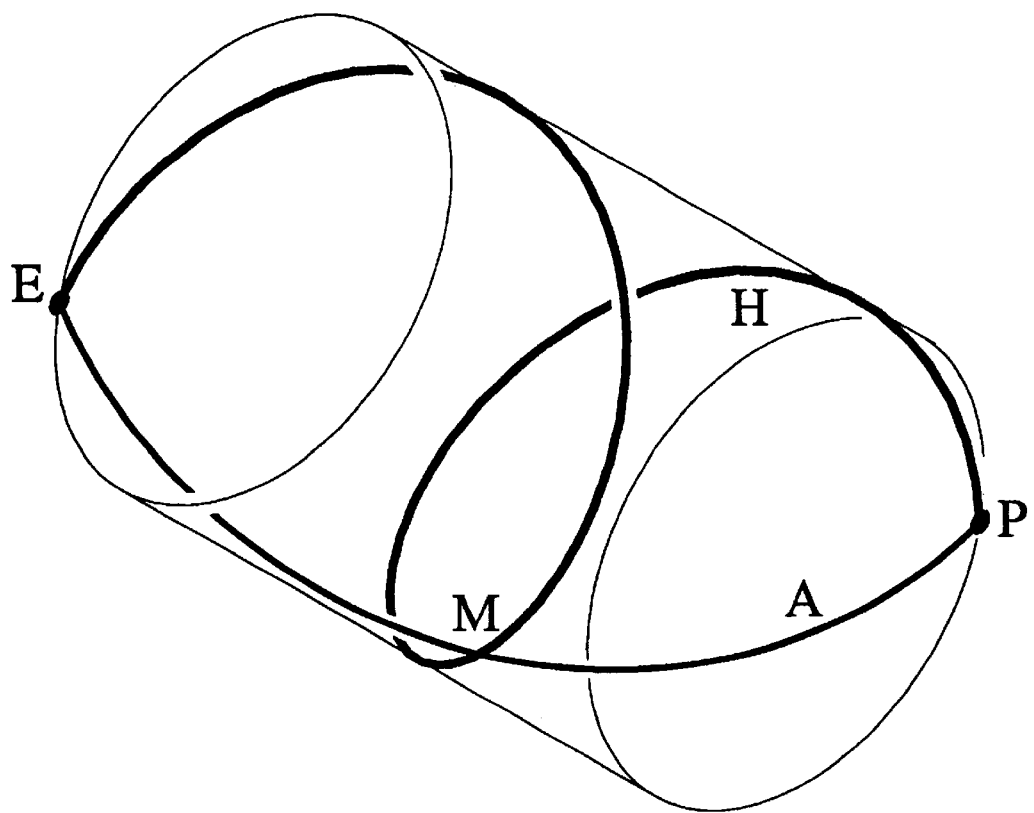
FIG. 15 is a mathematical diagram illustrating the determination of a helix by two end points, an intermediate point and the degree of twist.

When it is important to choose a particular entry point E on the skull or outer boundary of the brain, selecting E and the target P, FIG. 15, leaves three degrees of freedom in the choice of a helix. Fixing an intermediate point M determines two of these degrees of freedom; since there is a unique flat circular arc A through E, M and the target P, the remaining parameter essentially measures the out-of-plane twisting α of the helix chosen. The helix H can thus be selected by using the selection tool to choose M, and then adjusting α either by twisting the tool handle about its own axis, or by adjusting a slider. As well as being 'entry and intermediate' points, E and M could be chosen as co-targets with P for the action of the instrument.

Figure 16:
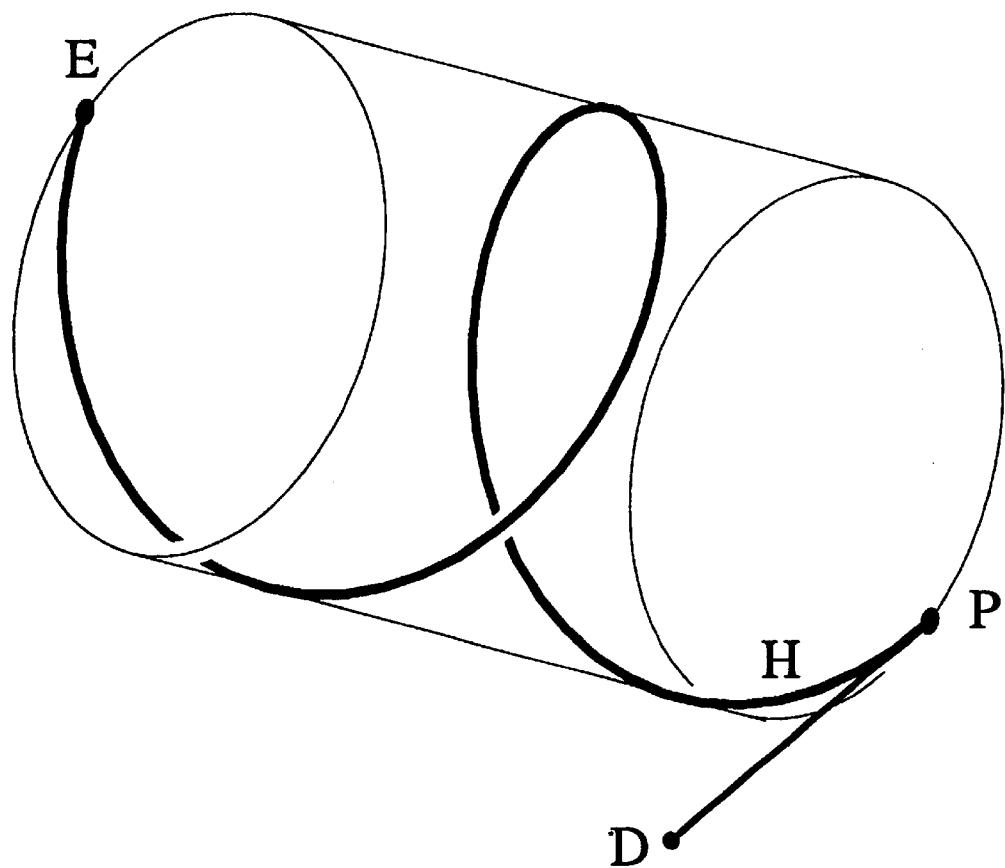
FIG. 16 is a mathematical diagram illustrating the determination of a helix by an end point, the direction of meeting it, another point, and the degree of twist.

Alternatively, one may wish to fix the entry point E, the target point P, and the tangential direction by which H approaches it, FIG. 16. This direction, easily controlled by moving the tip D of a line drawn from P, leaves one degree of freedom uncontrolled; by stipulating that the cylinder radius equal the length of the line PD, the system gives a correspondence between user movements of D and the set of helices joining P to E.

Figure 17:
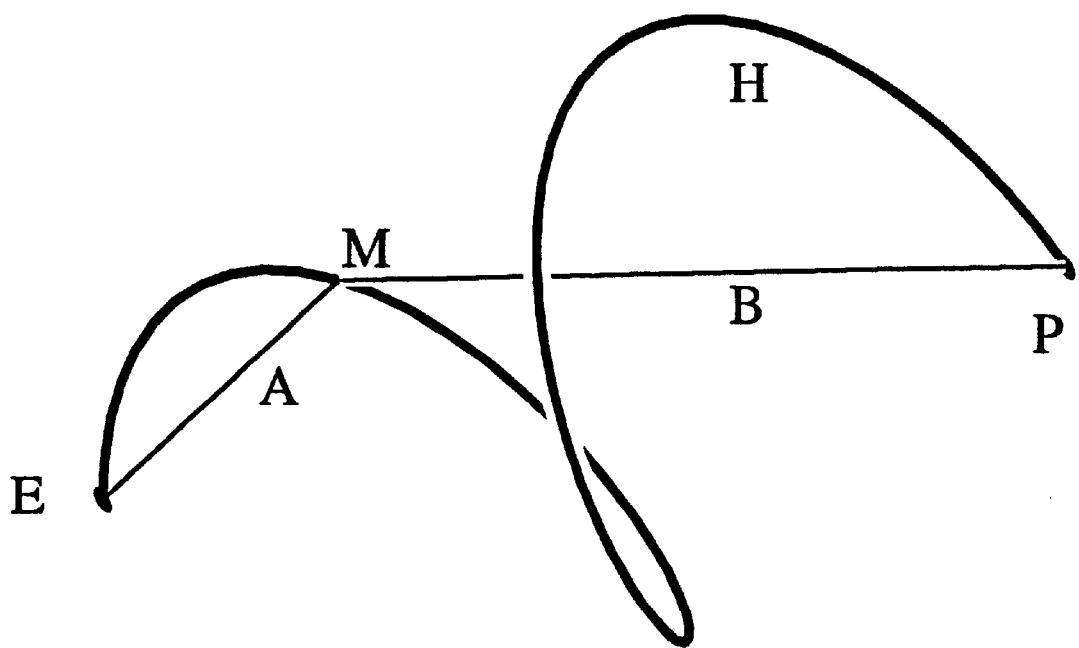
FIG. 17 is a mathematical diagram illustrating the determination of a helix by two end ends and an intermediate point.

Another such correspondence, FIG. 17, is created by using an intermediate point M, as in FIG. 15, but letting the total twist equal the logarithm of the ratio between the distances, A & B of M from E and P. This avoids the need for a separate twist control.

Figure 18:
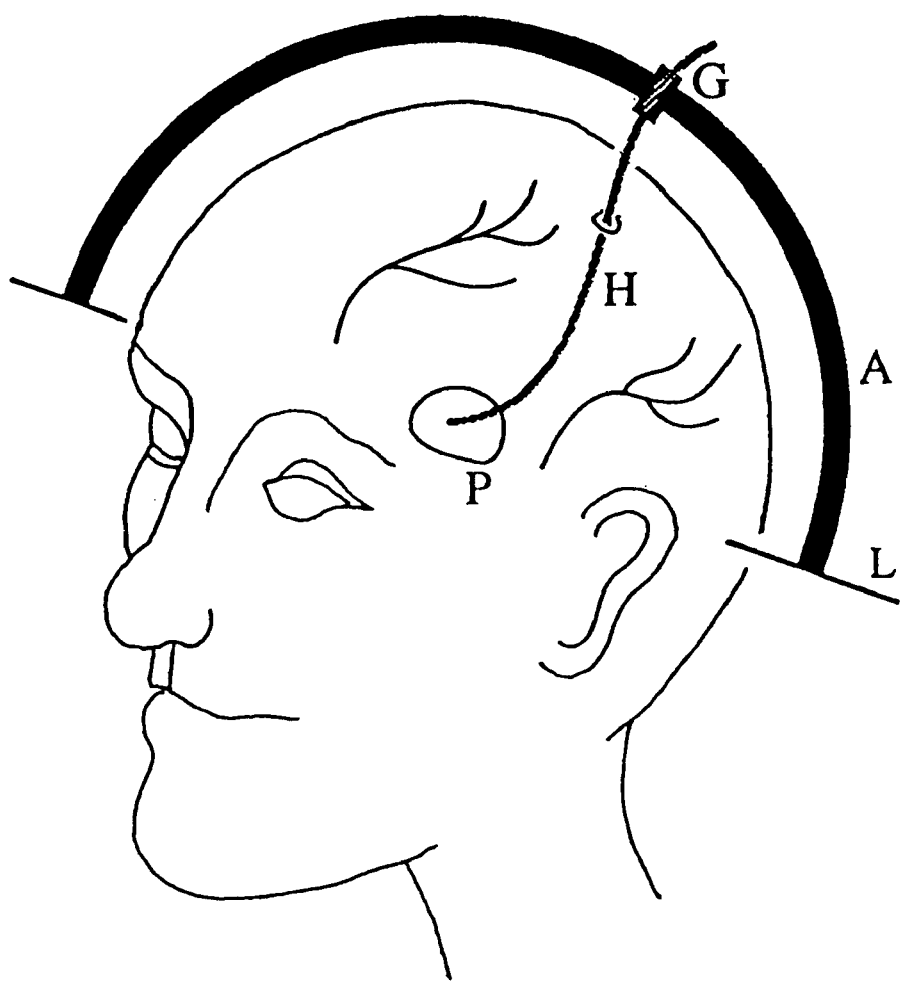
FIG. 18 is a mathematical diagram illustrating the determination of a helix by the settings of a mathematically modeled stereotactic frame.

Given a choice of target P and values for radius and pitch, and a position for the ring frame on which the arc A sketched in FIG. 18 is mounted, each possible position of the point G at which the guide block, discussed below, is rigidly attached to the frame corresponds to a unique choice of position for the helix H, for some angle of the arc with the axis L and angle on the arc at which the guide block is placed. Thus a frame model with widgets at G that can control radius and pitch, and G itself draggable from one point in space to another, provides a control scheme closely corresponding to actual mechanical settings, and thus particularly intuitive for frame users. It has the advantage that the widgets at G can be set to provide only radius and pitch values that are available in probe hardware at the site where the intervention is to be performed, avoiding the need for separate selection of the 'ideal helix' and then the best physically available approximation to it.

Techniques well known to those skilled in the art can detect which geometrical structures imported from a brain atlas as polyhedra are intersected by H, and highlight them to bring the fact to the user's notice. Inspecting the patient's scan data along the curve can be accomplished by a texture-based 'slicing tool' for the virtual reality apparatus environment.

In some instances, a number of the helices found by the chosen scheme for interaction may meet the minimum criteria. After a particular helix H has been selected, a detailed study should be conducted to determine the desirability of the particular helical path chosen, taking into consideration the various factors described above. Particularly, the helical path preferably should at least avoid most, if not all, of the sensitive surrounding areas, and intersect one of the intended opening sites.

The methods of mapping a curved path as described above may be applied in a wide range of stereotactic procedures, and generally the same or similar methods can be adopted regardless to the type of procedure being performed. However, each of the procedures may involve a different rigid surgical instrument. But regardless to the type and nature of the instrument, it must have the helical shape having the same pitch and radius as the helical path to utilize the useful properties of the helix.

Figures 10A, 10B:
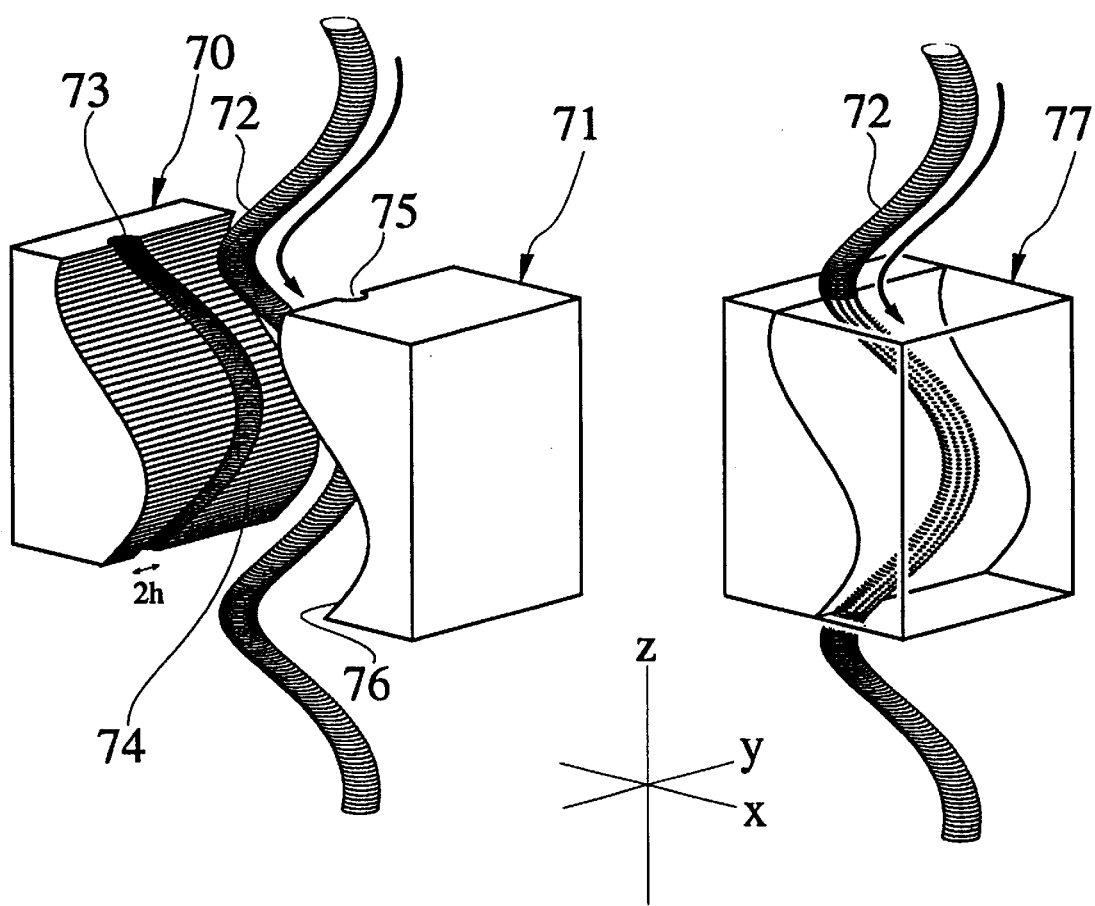
FIG. 10A shows a restraining block, in two parts, through which a rigid helical instrument can pass only by sliding along the helix defining the hole in the block.
FIG. 10B shows the restraining block of FIG. 10A where the two parts are mated into one piece.
Figure 11:
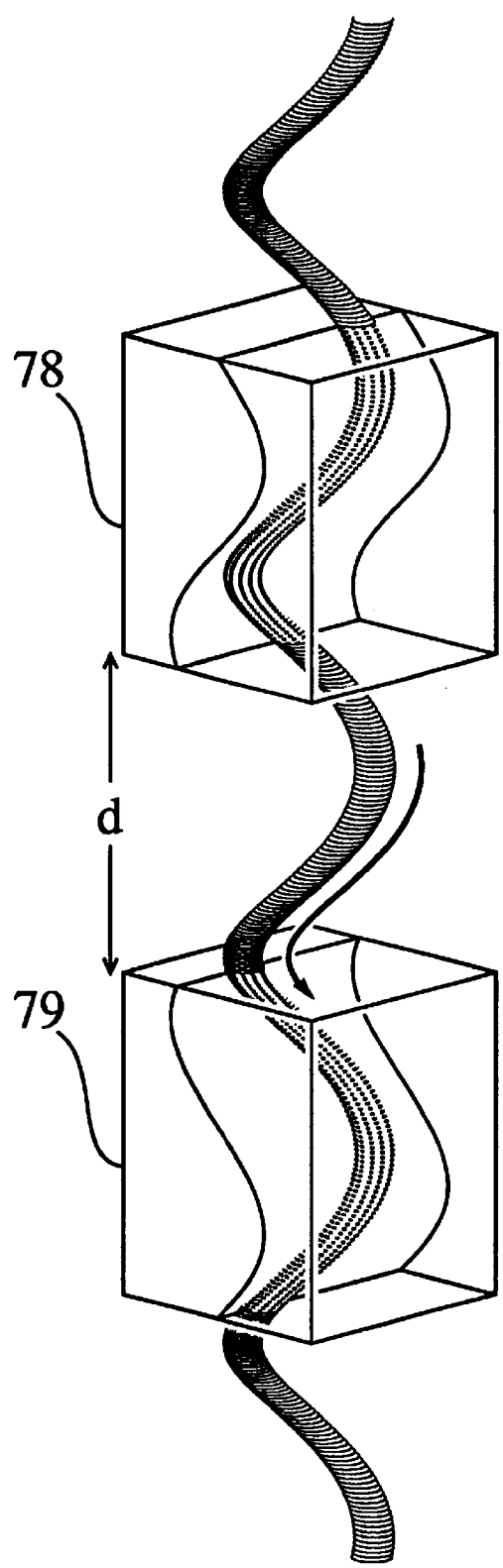
FIG. 11 shows a pair of restraining blocks through which a rigid helical instrument can pass only by sliding along the helix defining the holes in the blocks.
Figure 12:
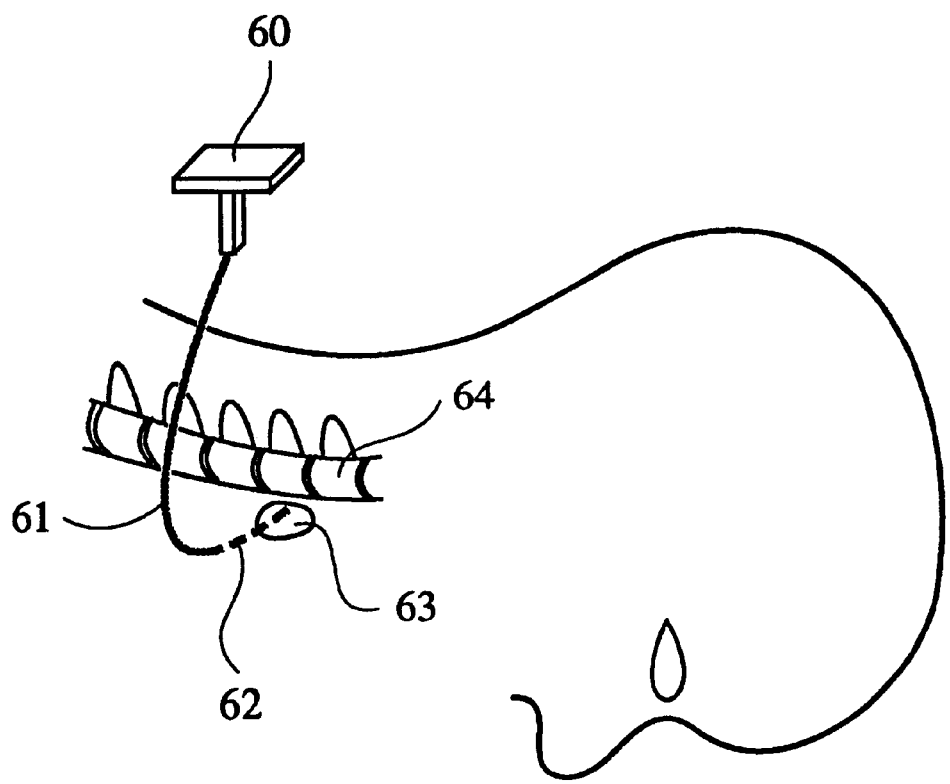
FIG. 12 shows a helical instrument being robot-guided along a helical path.

Furthermore, to drive a helical instrument along the path chosen, it must be rigidly held or constrained by a controller. A human or robot effector may move with it (as in FIGS. 12 and 13), holding it and moving with it; or its motion may be constrained by passing through a single or a plurality of guide blocks as illustrated in FIG. 10 and FIG. 11, respectively. FIG. 10A shows a block exploded into the two parts 70 and 71 in which it is most easily manufactured, with a helical instrument 72 between them. Two pieces of rigid metal, non-ferromagnetic if they are to be used in the presence of MR imaging devices, may be milled by a flat bed milling machine to the shapes shown; taking their common center as origin, suppose the helix has the parametrized form $$(x(s), y(s), z(s)) = (r\cos(s+p), r\sin(s+p), as)$$

where p defines the phase angle by which the helix is related to the x-axis where it passes through the (x,y) plane, and that the instrument has thickness 2h. Then from the material for part 70 one removes the material within h of any point (x(s), y(s), z(s)), creating a channel 73 through which the instrument will pass as shown by the curved arrow, and also the material with $$x > r\cos\left(\frac{z}{a} + p\right)$$

to create the surface 74 along which part 70 will meet 71. Similarly, in creating 71 one must remove the material within h of any point on the helix, creating part 75 of the hole through which the instrument will pass, and also the material with $$x < r\cos\left(\frac{z}{a} + p\right)$$

to create the surface 76 along which 71 will meet 70. The surfaces must be smoothly polished, for a close fit of the two parts and for smooth passage with minimal play for the helical instrument passing between them. Although the outer portions of the two parts are shown as rectangular, forming a combined rectangular guide block 77 in FIG. 10B, any other outer shape which may conveniently be clamped into a rigidly specified position may equally be used.

FIG. 11 shows a pair of such blocks with their phases p adjusted so that a helical instrument of the same radius, pitch and thickness will pass through both of them when they are clamped in line at an appropriate distance d; if the clamps can rotate about the helix axis by an angle A, this distance changes by the amount $$A\left(\frac{a}{2\pi}\right).$$

Such rotation would make it convenient for each block to be symmetrical about the axis of the helix it contains, but this is not otherwise necessary; where the radius r is large, and the helix not far from straightness, the block can be more practically sized if it the axis does not pass through it.

As the instrument is inserted first into a guide block, FIG. 10, or set of blocks FIG. 11, rigidly held by a robot or stereotactic frame, and then passes into a specimen, the guide block or set of blocks restricts the portion passing through it to a segment of a helical path (as a straight guide hole controls the direction of a straight needle), pushing the instrument compels its tip to move along the continuation of the same helical curve. Hence, as with a straight instrument, a surgeon can maneuver the instrument along a predetermined path, with damage only along that path. Pushing the instrument produces pressure at its tip, rather than along its sides. A high degree of agreement between planned and actual motion is thus possible. The same motion may be achieved by active constraint (FIG. 12), where a carefully planned 'wrist motion' of a robot effector 60 drives the instrument along its planned helical path 62 to reach a target 63 blocked for straight instruments by the spine 64. However, with present technology the passive constraint is the preferred implementation since (a) it is less costly to achieve a given degree of precision in such a constraint than in a robot with a six-degree-of-freedom effector, and (b) the surgeon pushing the instrument through the passive constraint can feel the tissue's degree of resistance to penetration, which can be a valuable sensory cue to what tissue the instrument is meeting, and hence whether insertion should continue.

The following is a sample of some of the stereotactic procedures which may utilize the mapping method described, and their corresponding instruments.

Figure 19:
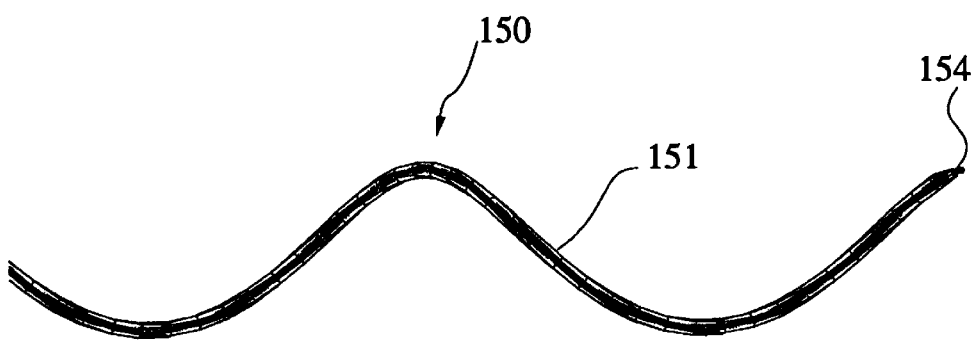
FIG. 19 shows a rigid helical monopolar electrode.
Figure 19A:
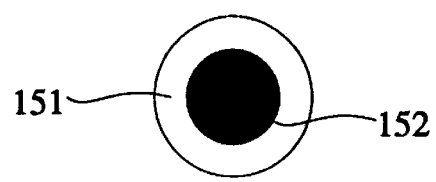
FIG. 19A is a cross-sectional view of the electrode in FIG. 19.

FIG. 19 shows a monopolar electrode 150, which may be used for measurement or to deliver small currents for stimulation or larger currents that flow through the tissue to a remote ground, applying heat on the way until the current is too spread to be significant: this is useful for such purposes as killing a tumor by heat, but the volume heated is too large and imprecisely defined for brain surgery. (It remains useful for work in, for example, muscle.) As illustrated in FIG. 19 and FIG. 19A, the instrument has an insulating rigid body 151 surrounding a conducting core 152, and a conducting tip 154.

Figure 20:
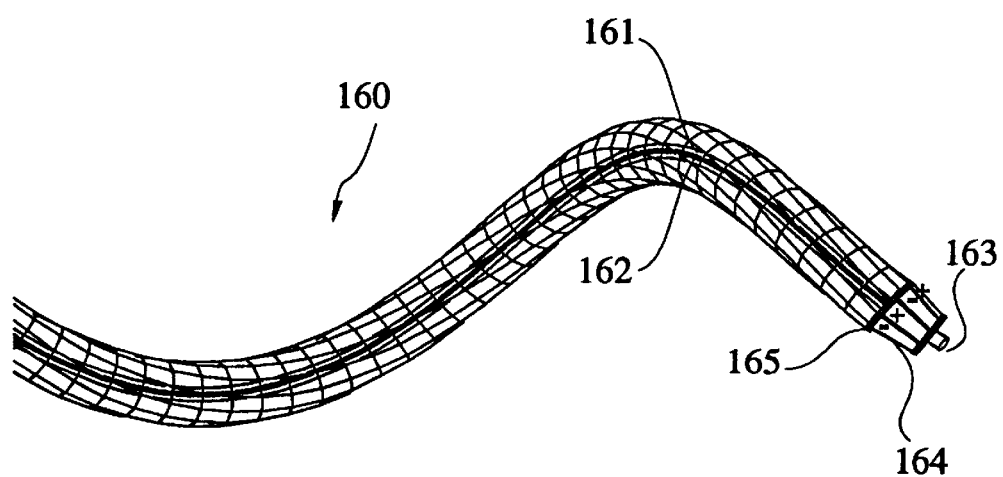
FIG. 20 shows a rigid helical bipolar electrode.

An important risk in stereotactic brain surgery is that of damage to a blood vessel. In open surgery the surgeon can detect such damage visually, and repair it by various methods; when an instrument is being driven through tissue, both detection and repair are more difficult. Two features will thus sometimes be desirable in a helical instrument intended for penetration of the brain: (a) detection of bleeding (by taking fluid samples, and examining them in situ or extracted via a tube), (b) cauterization using heat from bipolar electrical current. FIG. 20 shows a helical instrument 160 for facilitating a bipolar scheme, with a power cable 161 surrounding a fluid channel 162 supplying electrodes 164 of alternating polarity (marked + and −). The current then flows only very near the electrodes, which is useful for sharply localized work, and in particular for cauterizing a wound made by the instrument itself. The instrument has an opening for fluid samples 163, and electrodes 164 of alternating polarity around a non-conducting ring 165.

Figure 21A:
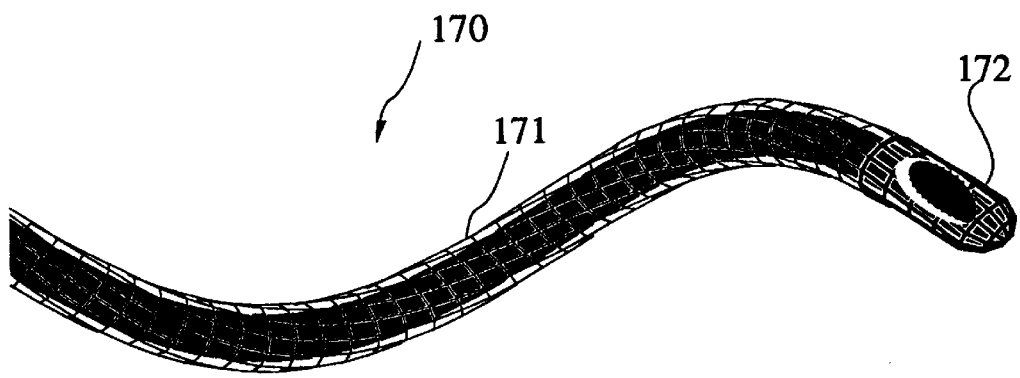
FIG. 21A is a perspective view of a helical biopsy sampling instrument.
Figure 21B:
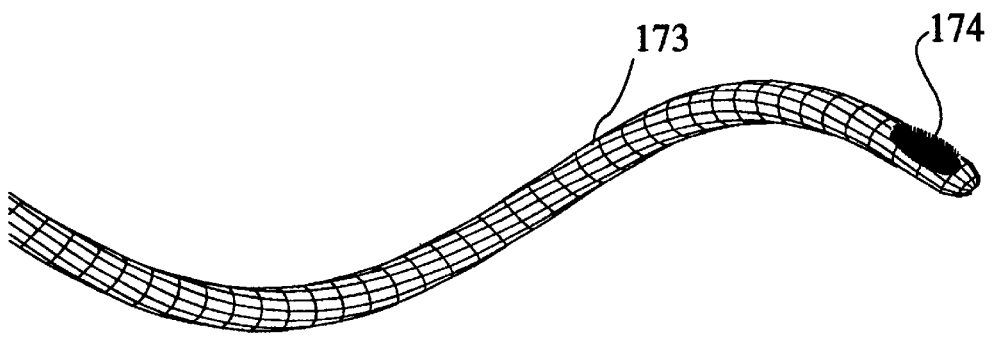
FIG. 21B is a perspective view of an inner shaft disposed inside the helical biopsy sampling instrument of FIG. 21A.

FIG. 21A illustrates a helical biopsy sampling instrument 170. It has a rigid curved tube 171 of a helical shape and a rotatable window head 172. As illustrated in FIG. 21B, the instrument 170 has a flexible, turnable, and withdrawable inner shaft 173 with a collection chamber for storing the sample. Rotating 173 within 172 opens and closes the chamber 174 relative to the position selected for the helix before insertion.

Figure 22:
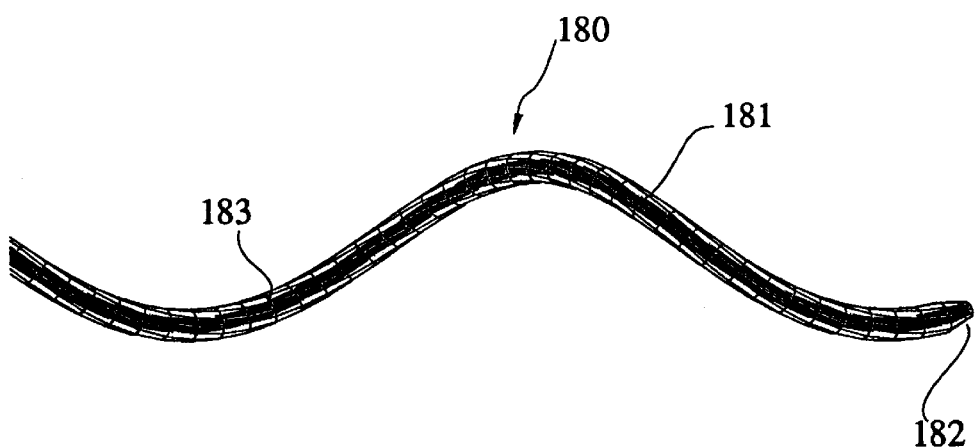
FIG. 22 is a perspective view of a helical needle for extraction or insertion of fluid.

FIG. 22 illustrates a helical needle which can be used to extract material for analysis (biopsy) or because it requires removal, or to deliver medicine or other fluids, to areas of the body where a straight needle would have difficulty in reaching. It has a hollow core 183 inside a rigid body 181, and a sharp point and an opening at the tip 182.

Figure 23A:
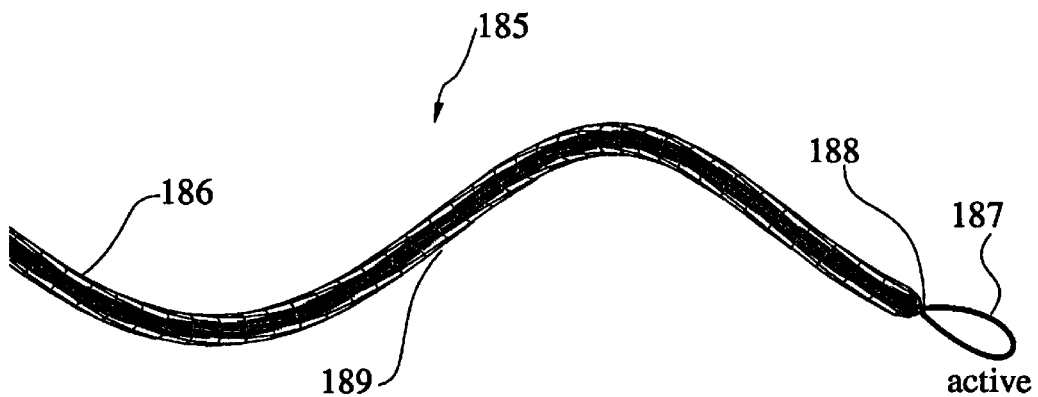
FIG. 23A is a perspective view of a helical surgical instrument with a resection loop in its active position.
Figure 23B:
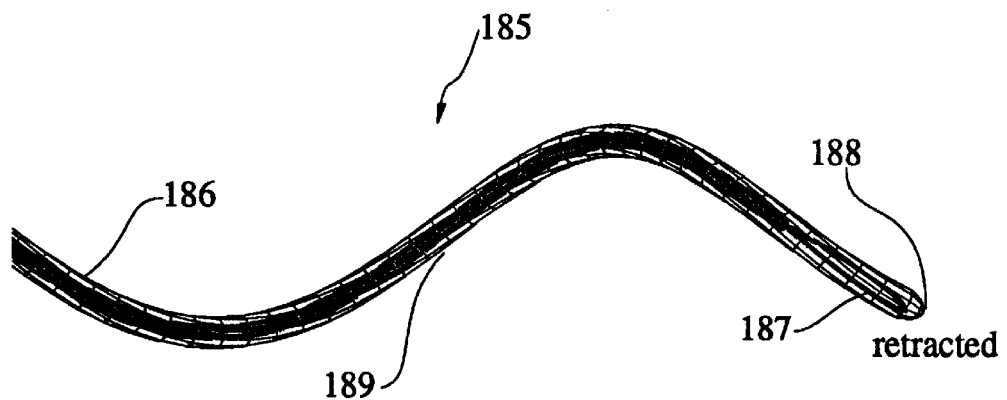
FIG. 23B is a perspective view of a helical surgical instrument with a resection loop in its retracted position.

FIG. 23A and FIG. 23B illustrate a resection instrument 185 having a rigid curved tube 186 with a flexible, turnable inner shaft 189. In the active position, FIG. 23A, the resection wire forms a loop 187 at the tip 188 of the instrument 185; in its retracted position, FIG. 23B, the loop 187 is closed and displaced inside the rigid tube 186.

Figure 24:
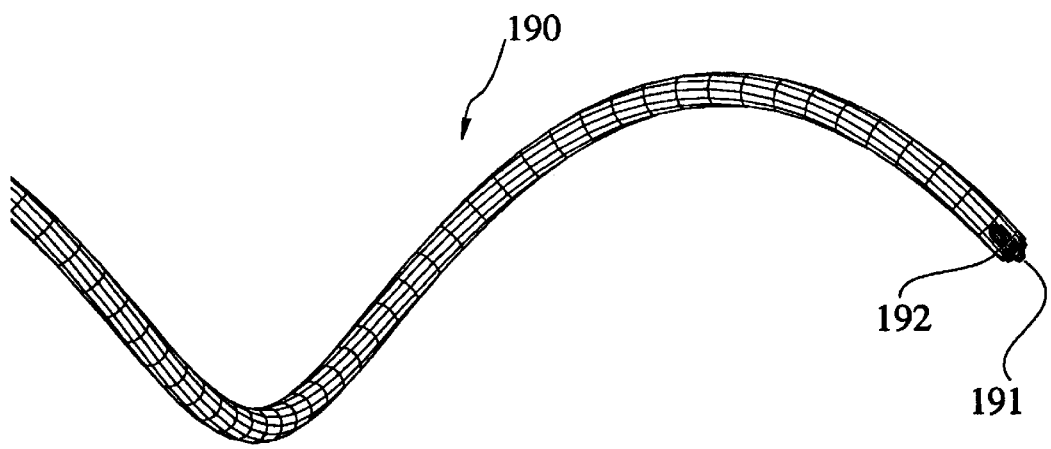
FIG. 24 is a perspective view of a helical temporary implant placement instrument.

FIG. 24 illustrates a temporary implant placement instrument 190 which can release radiation or drugs through the tip 191 of the instrument, from the material chamber 192.

Figure 25:
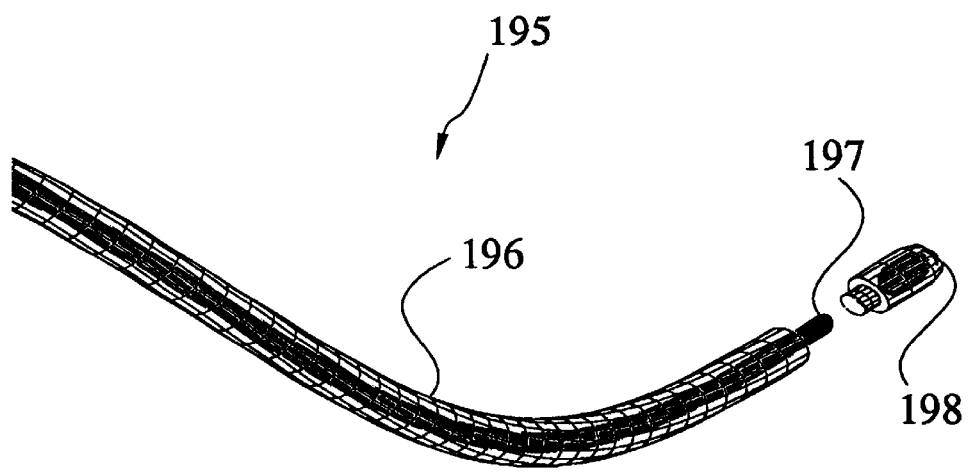
FIG. 25 is a perspective view of a helical permanent implant placement instrument.

FIG. 25 illustrates a permanent implant placement having a rigid outer tube 196, a rigid or flexible inner core 197 and a detachable drug source or device 198 at the tip, which can be pushed off by advancing the core 197.

Figure 26:
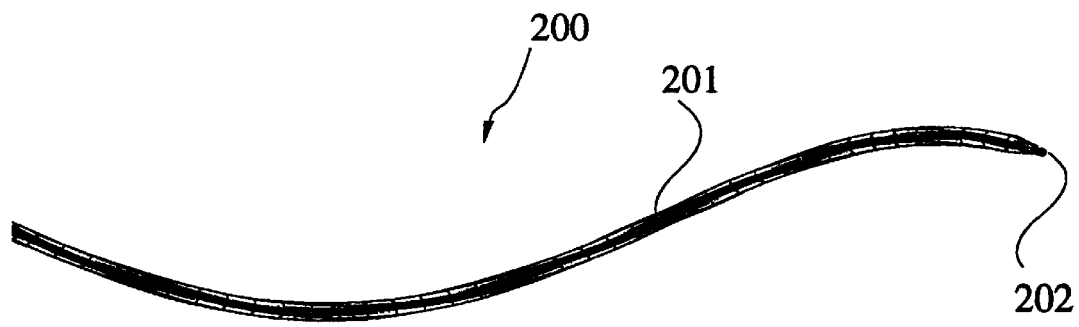
FIG. 26 is a perspective view of a helical instrument for delivering cold.

FIG. 26 illustrates an instrument 200 for cooling or heating an isolated area of a body. The instrument includes a cable or heat pipe core surrounded by an insulating sheath 201. At the tip is a thermocouple or pipe tip 202 for chilling.

Figure 27:
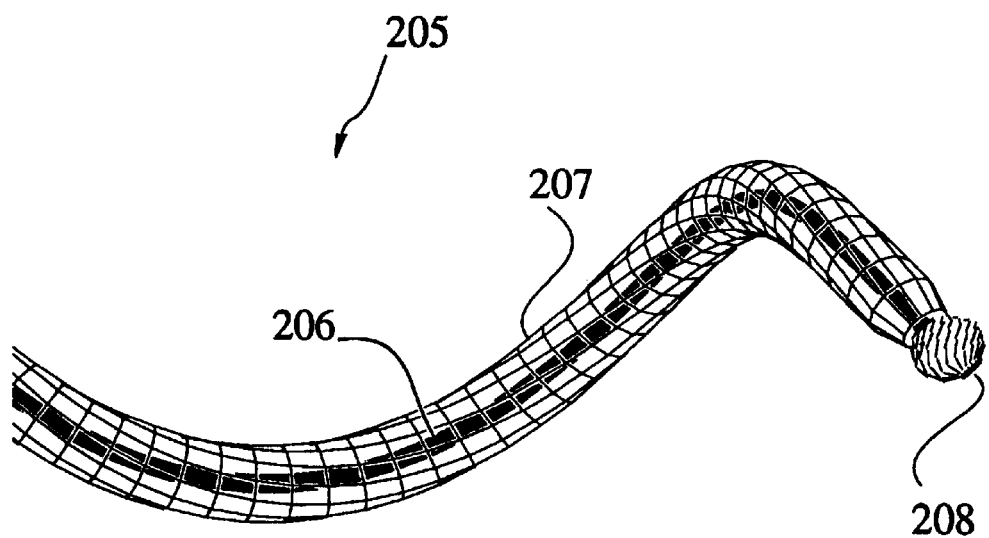
FIG. 27 is a perspective view of a helical instrument having a drilling tip.

FIG. 27 illustrates a drilling instrument 205 with a rotating flexible shaft 206 inside the rigid body 207 and a cutting burr 208 attached at its end.

Another use for a rigid helical penetrating instrument is in conjunctions with non-rigid ones; a class that includes catheters and endoscopes. A non-rigid instrument is guided by its surroundings, moving within fluid (most often blood or cerebrospinal fluid (CSF)) between the walls of the fluid space (most often a blood vessel or a ventricle). It can rarely be guided to push through parenchymal tissue in a planned way, even if it has a sharp tip, because flexibility allows it to turn aside at a wall or a variation in tissue resistance. This limits the points it can reach, and the routes by which it may arrive there. A rigid device, however, can be pushed through tissue, and even drill through bone (for instance, using an instrument illustrated in FIG. 27). This opens a channel which can then be exploited by a flexible device. This is currently a standard procedure with straight rigid instruments: a straight channel is pierced by a probe, reaching a cavity such as a ventricle and entering it in a convenient direction; it is then withdrawn, and a flexible instrument pushed in through the channel that has been opened. This flexible instrument can then follow the cavity by the usual mechanics of such instruments, reaching a target without further tissue damage.

Figure 28:
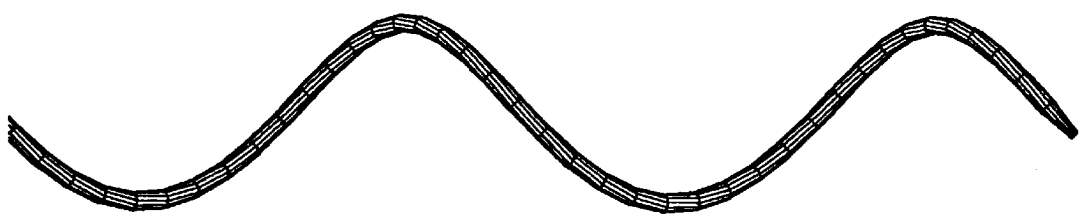
FIG. 28 is a perspective view of a helical instrument used solely for piercing.
Figure 29:
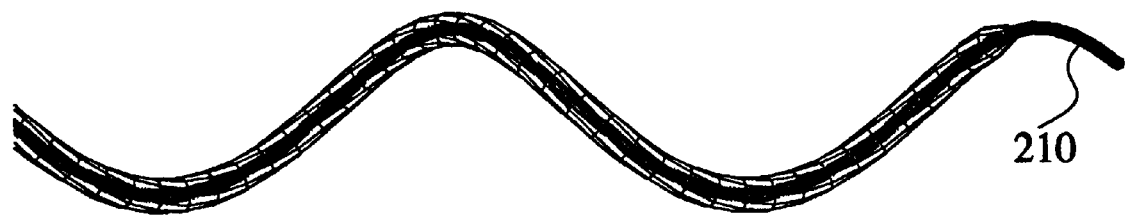
FIG. 29 is a perspective view of a helical instrument having a guide wire.
Figure 30:
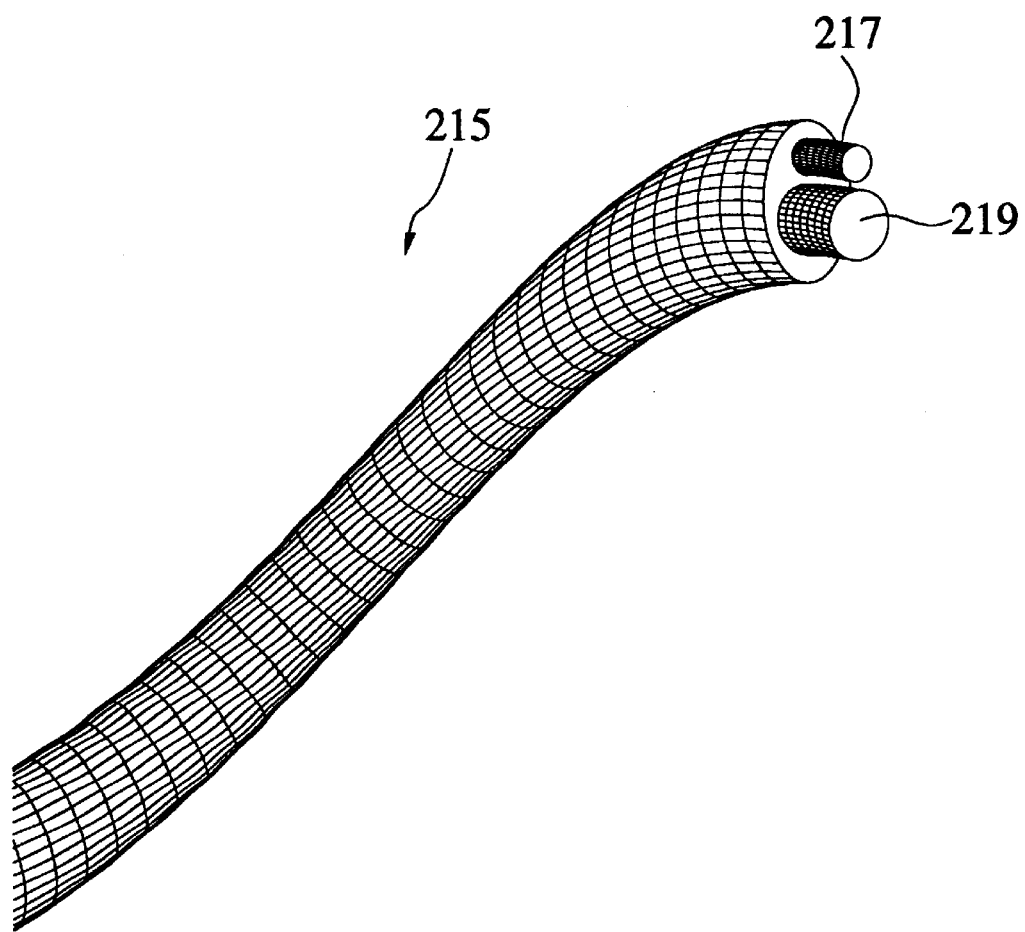
FIG. 30 is a perspective view of a helical instrument having a guide wire in addition to a core serving another instrumental function.

The use of a helical instrument increases the options in such channel creation. This may be done by simply piercing the tissue with a helical instrument as illustrated in FIG. 28, that is a simple penetrating device; but in some cases the flexible instrument may not follow the resulting channel accurately, since it must flex to do so. In this case it is appropriate to pierce with a hollow helical instrument shown in FIG. 29 down which a flexible guide wire 210 can be inserted. When the channel has been created, the surgeon can remove the helical instrument while leaving the guide wire 210 in place, and then slide a flexible instrument along it. (A channel to contain a guide wire is a common feature of the design of such flexible instruments, but the 'Seldinger technique' of using a guide wire to change the instrument that follows a given path has not been extended to paths created by rigid instruments, which have been only straight.). A guide wire channel 217 may also be included in a rigid helical instrument 215, illustrated in FIG. 30, containing a channel 219 serving the passage of energy, electrical current, or biological/therapeutic material, in either direction.

A helically opened channel may be useful in endoscopic work, even where there is already an access to some cavity for flexible instruments, since it is often necessary to have several instruments simultaneously in place: light, camera, and active tools guided by what is seen in the camera view. Both to avoid overcrowding the access path, and to gain a more felicitous set of relative positions of these devices, there is use for delivering some of them by helical paths created by rigid insertion, rather than by insertion of a flexible catheter. The extra degrees of freedom provided by a helix over a straight path will allow the surgeon more freedom in the setting up of positions, with less damage in arriving there. The helical implements useful in such work will include: scissors, by which tissue can be cut; nibblers, by which bone or tissue can be cut away; forceps, by which tissue can be grasped; and spreaders, by which tissue can be forced apart.

Figure 31:
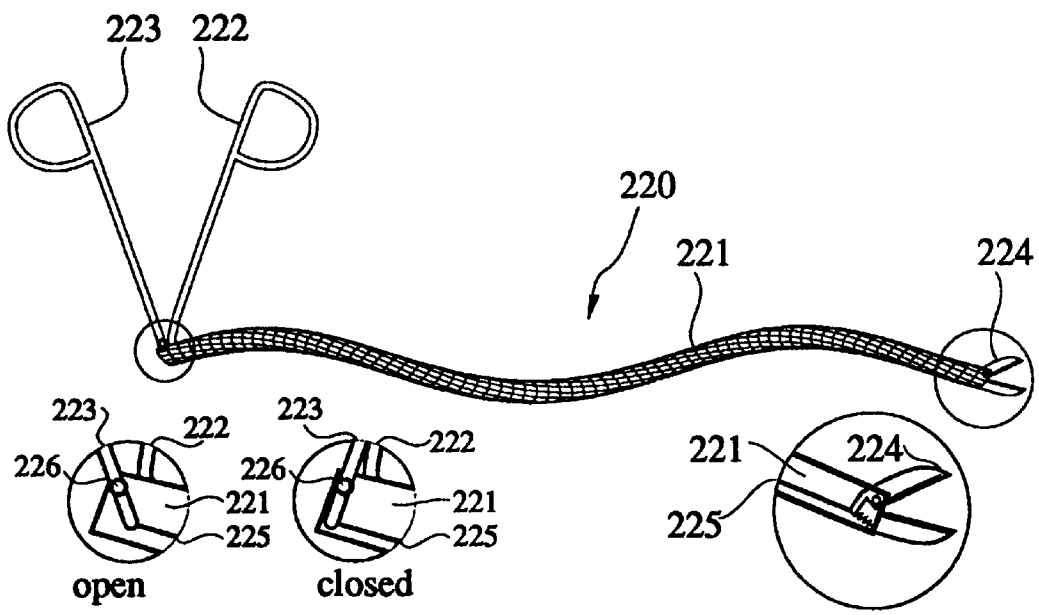
FIG. 31 is a perspective view of a helical surgical instrument with a cutting tool, gripping, spreading or clipping tip.
Figure 31A:
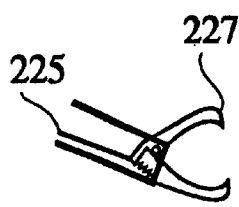
FIG. 31A is a perspective view of a nibbling tool for the helical instrument illustrated in FIG. 31.

FIG. 31 illustrates an instrument 220 having a rigid, helical tube 221, a fixed hand grip 222, a turning hand grip 223, and a cutting tool 224. A wire 225 is attached to the hand grip 223 and to the cutting tool 224. The cutting tool 224 can be made to open and close by rotating the hand grip 223 around its pivot 226 as demonstrated by the two exploded views. Various other tools may be attached to the instrument 220 in place of the cutting tool 224, such as the nibbling tool 227 in FIG. 31A; a gripping tool 228 in FIG. 31B; and the spreading tool 229 in FIG. 31C.

Figure 32:
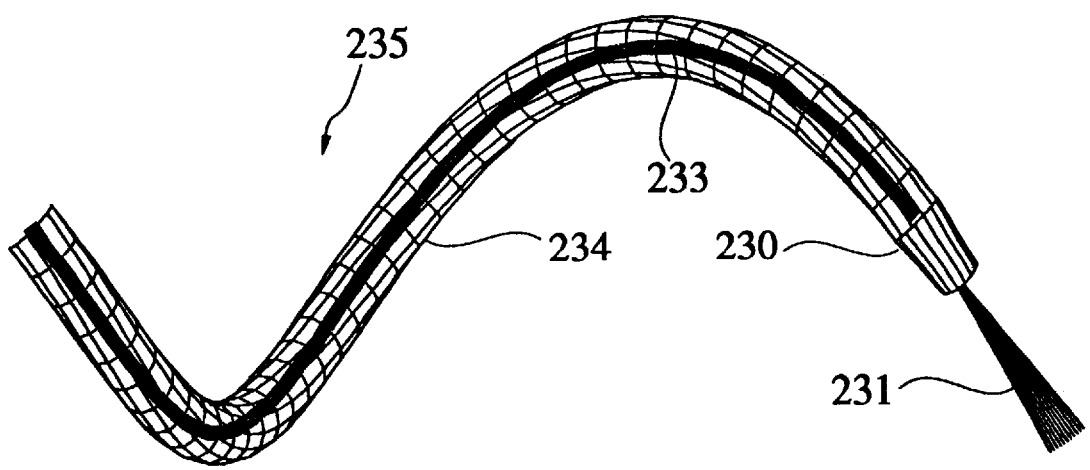
FIG. 32 is a perspective view of a helical surgical instrument with a laser tip.

FIG. 32 illustrates a helical instrument with a steerable laser tip 230 which is fed by a cable 234 in a rigid helical body 235. The laser delivers highly localized radiation 231 with which to burn away unwanted material, separate tissues, or cauterize wounds.

Figure 33:
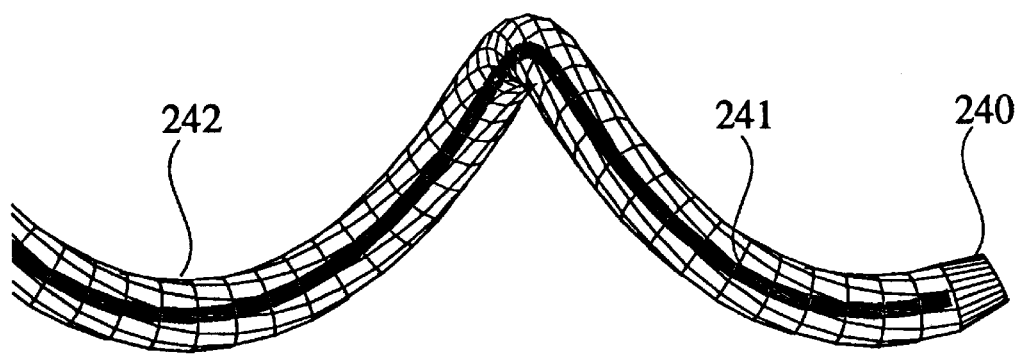
FIG. 33 is a perspective view of a helical endoscopic instrument.
Figure 34:
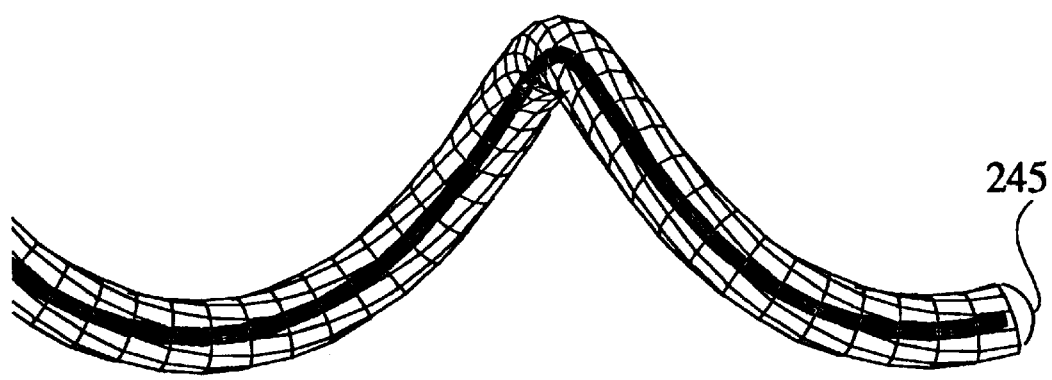
FIG. 34 is a perspective view of a helically mounted light source.

FIG. 33 illustrates an endoscope with a camera 240 at its tip and an electrical or optical fiber connection 241 disposed inside a rigid body 242. An endoscope requires light to see by, preferably lighting the view from the side. FIG. 34 shows a light casting tip 245.

Figure 31B:
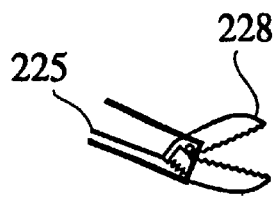
FIG. 31B is a perspective view of a gripping tool for the helical instrument illustrated in FIG. 31.
Figure 31C:
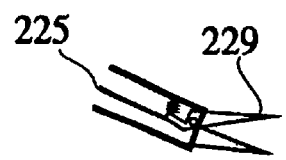
FIG. 31C is a perspective view of a spreading tool for the helical instrument illustrated in FIG. 31.
Figure 35:
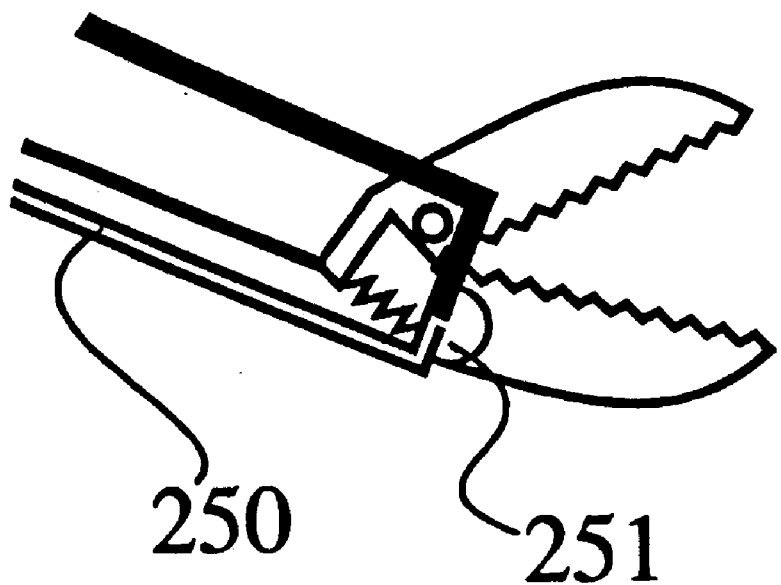
FIG. 35 shows the combination of a light delivery channel with a helical tube serving another function.

FIG. 35 illustrates the incorporation of an optic fiber or power channel 250 for a light source 251 shedding light on the action of an implement such as the gripper shown in FIG. 31B (placed on both sides of the gripper jaw), reducing the number of separate instruments that must enter the brain. Such a lighting feature may be added to any of the instruments here described.

Figure 36:
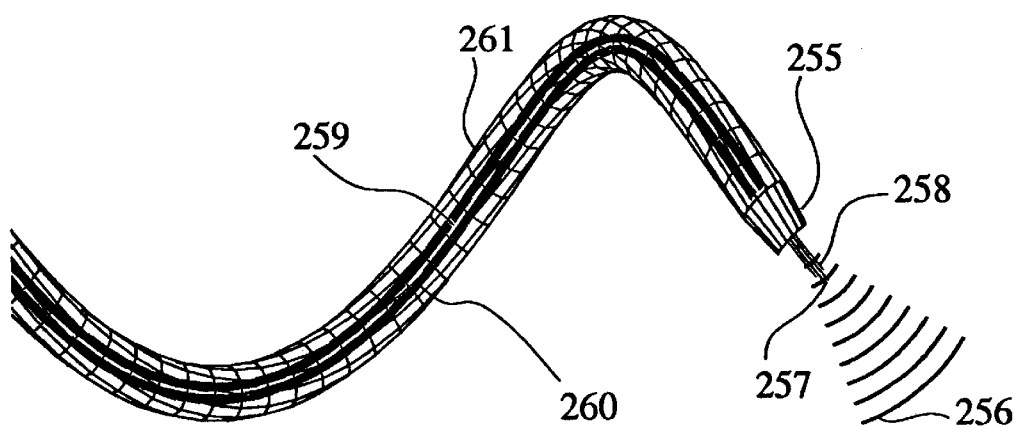
FIG. 36 is a perspective view of a helical instrument for delivering pulverizing.

FIG. 36 illustrates an ultrasonic aspirator, with a vibrating source 255 of directed ultrasound 256 to pulverize tissue, a liquid insertion tube 257 to make a slurry of it, an extraction tube 258 by which to suck out the result, and fluid channels 259 with the power channel 260 inside the rigid helical tube 261.

Figure 37:
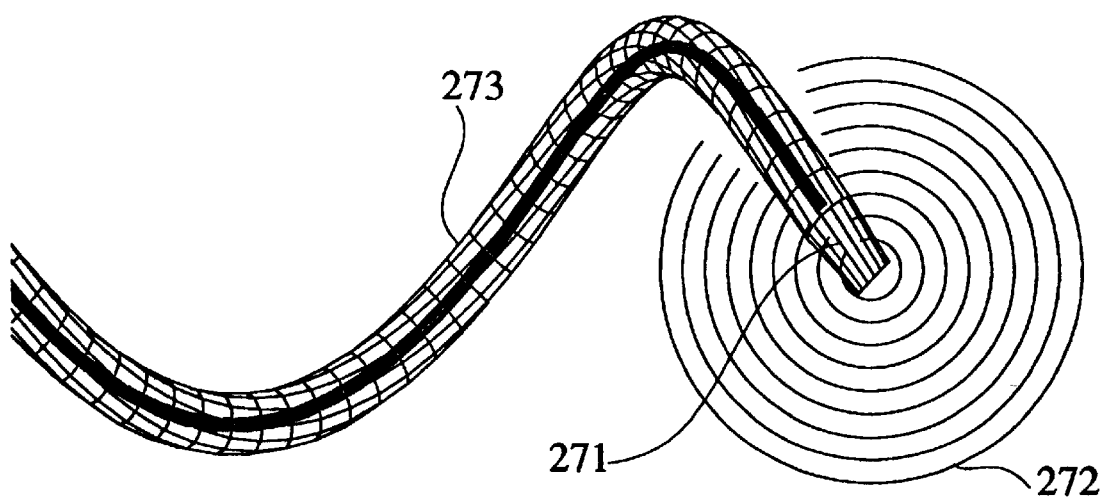
FIG. 37 is a perspective view of a helical instrument for delivering low intensity ultrasound for imaging purposes.

FIG. 37 illustrates a source 271 of lower intensity ultrasound 272, so that ultrasound receivers elsewhere can collect data from which a detailed image of the region around the source can be reconstructed.

It should be understood by those skilled in the art that the above list of applications is presented here only as a way of illustrating the wide range of ways that the present invention can be used, and therefore, should not be construed as being a complete list of the possible application. Hence, various modifications, additions and substitutions are possible for the invention described herein, without departing from the scope and spirit of the invention as disclosed in the accompanying claims.

We claim:

1. A method of mapping a curved path for stereotactic surgery using a rigid stereotactic surgical instrument to access an area of a patient's body comprising:
   a) obtaining an accurate image of an area of the body, said image including an opening site and a target region;
   b) determining high-risk areas around said target region;
   c) selecting a non-linear curve within said image, wherein said non-linear curve is substantially helical in shape along an entirety of a curved path extending between the opening site and the target region; wherein said non-linear curve intersects said target region and said opening site but not said high-risk areas, said non-linear curve defining the curved path for which a rigid stereotactic surgical instrument having an identical shape to said non-linear curve is navigable to said target region;
   d) providing a rigid stereotactic surgical instrument with a rigid tip; and
   e) inserting the rigid stereotactic surgical instrument along the curved path selected in step (c) with the tip of the rigid stereotactic surgical instrument tracing said non-linear curve.

2. The method as recited in claim 1, wherein the non-linear curve in said selection step c) is a helix.

3. The method as recited in claim 2, wherein said selecting step c) includes:
   i) marking a target point P in said target region;
   ii) selecting straight line L as a helix axis; and
   iii) tracing said non-linear curve around said line L maintaining a constant radius r and angle a with respect to said line L; said non-linear curve intersecting said target point P.

4. The method as recited in claim 3, wherein said selecting step c) and said tracing step e) are performed substantially simultaneously.

5. The method as recited in claim 1, wherein said image obtaining step a) is performed using an imaging technique selected from the group of MRI, PET, CAT, plain radiography, SPECT, MEG, EEG, US, fMRI, angiography, color doppler, and reference maps of the body.

6. The method as recited in claim 5, further comprising the steps of digitizing said image creating a digitized image, and interfacing said digitized image with a computer.

7. The method as recited in claim 1, wherein the selecting step c) is performed immediately upon completion of the determining step b).

8. The method as recited in claim 7, wherein a virtual reality apparatus is used to execute at least one of the steps.

9. A method of mapping a curved path for stereotactic surgery using a rigid stereotactic surgical instrument, said method being aided by a virtual reality apparatus, said virtual reality apparatus including a display means, and a stylus for allowing a user to interact with said virtual reality apparatus via said display means, said virtual reality apparatus comprising means for displaying medical images on said display means and superimposing a helical curve of a selected radius r and angle within said images, said method comprising:
   a) displaying an accurate image of an affected area of a patient's body on said display means, said image including a target region;
   b) determining high risk areas around said target region;
   c) pointing said stylus to a point P in said target region;
   d) moving said stylus until a helical curve from point P to an entry point into the patient is displayed on said display means such that no part of the helical curve intersects said high risk areas, said helical curve defining a curved path for which a rigid stereotactic surgical instrument having an identical shape as said helical curve is navigable to said target region.

10. The method as recited in claim 9 further comprising:

e) determining a location for an opening site;

f) determining whether said helical curve intersects the opening site; and g) moving said stylus and selecting another helical curve which does not intersect said high-risk areas but intersects said opening site.

11. A method of mapping a least invasive curved path for stereotactic surgery using a rigid stereotactic surgical instrument comprising:

obtaining an accurate image of an affected area of a patient's body, said image including a target region and an opening site;

determining high-risk areas around said target region;

assigning a medical acceptability value to each of said high-risk areas;

selecting a plurality of curves within said image wherein each of said plurality of curves is helical in shape, and said plurality of curves intersecting said target region and said opening site;

assigning a medical acceptability value to each of said plurality of curves based on its interaction with said high-risk areas;

comparing said plurality of curves based on said medical acceptability value; and choosing a curve with an optimal value, said curve defining a curved path for which a rigid stereotactic surgical instrument having an identical shape as said curve is navigable to said target region.

12. A method of mapping a curved path for intracranial stereotactic surgery using a rigid stereotactic surgical instrument comprising:

obtaining an accurate image of an affected area of a patient's intracranial area, said image including a target region and an opening site;

determining high-risk areas around said target region;

selecting a curve within said image wherein said curve is helical in shape, wherein said curve intersects said target region and said opening site, but not said high-risk areas, said curve defining a curved path for which a rigid stereotactic surgical instrument having an identical shape as said curve is navigable to said target region.

* * * * *